United States Patent
Luthe et al.

(10) Patent No.: US 10,960,096 B2
(45) Date of Patent: Mar. 30, 2021

(54) GAS-PERMEABLE DEVICES WHICH ABSORB VOC AND/OR POLLUTANTS AND/OR ARE BIOCIDAL, AND USE THEREOF

(71) Applicant: WINDPLUSSONNE GMBH, Gronau (DE)

(72) Inventors: Gregor Luthe, Gronau (DE); Nele Schmidt, Ahaus (DE); Reinhard Gausling, Heek (DE); Matthias Bischoff, Gronau (DE); Bernfried Schroeder, Ahaus (DE)

(73) Assignee: WINDPLUSSONNE GMBH, Gronau (DE)

( * ) Notice: Subject to any disclaimer, the term of this patent is extended or adjusted under 35 U.S.C. 154(b) by 253 days.

(21) Appl. No.: 16/094,457

(22) PCT Filed: Apr. 18, 2017

(86) PCT No.: PCT/EP2017/000491
§ 371 (c)(1),
(2) Date: Oct. 17, 2018

(87) PCT Pub. No.: WO2017/182120
PCT Pub. Date: Oct. 26, 2017

(65) Prior Publication Data
US 2019/0125914 A1    May 2, 2019

(30) Foreign Application Priority Data
Apr. 19, 2016 (DE) .......................... 102016004570.1

(51) Int. Cl.
*A61L 9/014*   (2006.01)
*B32B 27/20*   (2006.01)
(Continued)

(52) U.S. Cl.
CPC .............. *A61L 9/014* (2013.01); *A01N 25/08* (2013.01); *A01N 59/16* (2013.01); *B01D 53/02* (2013.01);
(Continued)

(58) Field of Classification Search
None
See application file for complete search history.

(56) References Cited

U.S. PATENT DOCUMENTS 5,883,025 A   3/1999   Karstens et al.
6,020,369 A   2/2000   Schinazi et al.
(Continued)

FOREIGN PATENT DOCUMENTS

AT   396591 B     10/1993
DE   3622933 A1   1/1987
(Continued)

OTHER PUBLICATIONS

International Preliminary Report on Patentability for International Application No. PCT/EP2017/000491 filed Apr. 18, 2017 on behalf of Windplussonne GMBH. dated Nov. 1, 2018. 14 pages (English Translation + German Original).
(Continued)

*Primary Examiner* — Jelitza M Perez
(74) *Attorney, Agent, or Firm* — Steinfl + Bruno LLP

(57) ABSTRACT

Gas-permeable devices which absorb VOC and pollutants and/or are biocidal, containing molded parts or consisting of molded parts, containing materials or consisting of materials on the basis of wood, biodegradable fibers, biodegradable films and/or separated manure, containing geometrically regular and/or irregular, free and/or aggregated and/or agglomerated carbon nanoparticles, carbon microparticles and/or carbon macroparticles. Carbon is selected from the group consisting of biocarbons, biochar, charcoal, screening
(Continued)

residues of charcoal, wood ash, activated carbons, hard coal, animal charcoal, carbons from animal waste, pyrogenic carbon having different degrees of pyrolysis, functionalized carbons, pretreated carbons, washed carbons, and extracted carbons.

10 Claims, 6 Drawing Sheets

(51) Int. Cl.
  *B01J 20/24* (2006.01)
  *B01J 20/20* (2006.01)
  *B01J 20/28* (2006.01)
  *A01N 59/16* (2006.01)
  *B01D 53/02* (2006.01)
  *B01J 20/30* (2006.01)
  *A01N 25/08* (2006.01)
  *B01J 20/10* (2006.01)

(52) U.S. Cl.
  CPC ............... *B01J 20/10* (2013.01); *B01J 20/20* (2013.01); *B01J 20/24* (2013.01); *B01J 20/28004* (2013.01); *B01J 20/28026* (2013.01); *B01J 20/3042* (2013.01); *B32B 27/20* (2013.01); *A61L 2209/14* (2013.01); *A61L 2209/22* (2013.01); *B01D 2253/102* (2013.01); *B01D 2257/708* (2013.01); *B32B 2264/108* (2013.01); *Y10T 428/25* (2015.01)

(56) References Cited

U.S. PATENT DOCUMENTS

| | | | |
|---|---|---|---|
| 6,403,699 | B1 | 6/2002 | Roeckrath et al. |
| 2014/0109796 | A1 | 4/2014 | Evers et al. |
| 2015/0027179 | A1 | 1/2015 | Josse et al. |
| 2015/0298346 | A1 | 10/2015 | Borowka et al. |

FOREIGN PATENT DOCUMENTS

| | | |
|---|---|---|
| DE | 19517763 A1 | 11/1996 |
| DE | 19722324 A1 | 12/1998 |
| DE | 202014004445 U1 | 6/2014 |
| EP | 0008127 A1 | 2/1980 |
| EP | 0116414 A1 | 8/1984 |
| EP | 0249201 A2 | 12/1987 |
| EP | 0276501 A2 | 8/1988 |
| EP | 2727691 A1 | 5/2017 |
| MY | 129849 A | 5/2007 |
| WO | 94/22968 A1 | 10/1994 |
| WO | 97/12945 A1 | 4/1997 |

OTHER PUBLICATIONS

International Search Report for International Application No. PCT/EP2017/000491 filed Apr. 18, 2017 on behalf of Windplussonne GMBH. dated Aug. 10, 2017. 7 pages (English Translation + German Original).

Adler H.J. et al., "Rompp Lexikon Lacks and printing inks" Georg Thieme Veda: Stuttgart pp. 250-252 1998 (Original + Partial English) 5 pages.

Behler A, et al., "Wetting Agents" Thieme Rompp Online Apr. 2014 (Original + Partial English) 2 pages.

Draper K, et al., "Paper from Plant Charcoal" Ithaca Journal 2015 (Original + Partial English) 7 pages.

Schmidt H.P. et al., "55 Uses of Plant Charcoal" Ithaca Journal pp. 92-102 Jan. 2012.

Written Opinion for International Application No. PCT/EP2017/000491 filed Apr. 18, 2017 on behalf of Windplussonne GMBH. dated Aug. 10, 2017. 10 pages (English Translation + German Original).

GAS-PERMEABLE DEVICES WHICH ABSORB VOC AND/OR POLLUTANTS AND/OR ARE BIOCIDAL, AND USE THEREOF

CROSS REFERENCE TO RELATED APPLICATIONS

The present application is the US national stage of International Patent Application PCT/EP2017/000491 filed on Apr. 18, 2017 which, in turn, claims priority to German application 102016004570.1 filed on Apr. 19, 2016.

FIELD OF THE INVENTION

The present invention relates to VOC and/or pollutant absorbing and/or biocidal gas permeable devices.

Furthermore, the present invention relates to the use of devices for the purification of gases, in particular air, of VOC, pollutants and/or harmful microorganisms.

BACKGROUND

The prior art cited in the present application is incorporated herein by reference.

Wood materials can consist of different types of comminuted wood, which differ in size, shape, position and/or arrangement. The production of, for example, plate and/or rod-shaped wood material is carried out by mixing the different wood particle shapes with natural and/or synthetic binders, such as adhesives, and/or addition of other additives, wood preservatives and/or color particles. Subsequently, the mixed materials are produced to become plate and/or rod-shaped wood materials in a hot and/or cold pressing, in a casting and/or bulk method.

Various types of wood-based materials are, for example:
Solid wood materials and/or materials based on solid wood
    solid wood and/or glued wood panels
    glued laminated timber and/or other board stacking construction
    blockboard
    laminated wood and/or other solid wood elements glued together
Veneer materials
    veneered plywood (FU)
    laminated veneer lumber
    strand lumber
    bending plywood
    synthetic resin (KP)
Wood chipboard
    flat press plate (P2)
    extruded plate
    veneer molded parts
    coarse chipboard (OSB board)
    chipboard wood (LSL)
Wood fiber materials
    wood fiber insulation board (HFD)
    medium hardboard (MB)
    hard fiberboard (HB and HFH)
    medium density fiberboard (MDF)
    high density fiberboard (HDF)
Composites
    wood plastic composites, also called wood-polymer materials
    lightweight panels
    laminated densified wood
    Arboform Furthermore, there are gypsum fiber boards, Rigidur H10® and Rigidur H Active Air®, which consist of gypsum, paper fibers and mineral aggregates. These gypsum fiber boards are breathable and absorb pollutants and so-called VOCs.

Coal refers to a black and/or brownish-black, solid sedimentary rock formed by carbonation.

The uses of coal are broad and no longer limited to agriculture. Coal is being integrated into more and more fields of application and its positive properties are being exploited.

Coal is used in the paper industry, with a maximum load of 30%.

The present applications of coal are schematically and exemplarily listed:

food and beverage packaging: coffee mugs, pizza boxes, banana boxes, coffee filters, food containers, egg cartons, fruit bags, napkins, placemats, take-away containers, sandwich wrapping paper, disposable dishes courtyard and garden: growing pots, seed tape, mulch band, germination protection, leaves dust bags, plant packaging, weed fleece, soil housewares: book covers, garment boxes, wallpaper, furniture, bedding, passepartouts, office and shipping articles: pouches, boxes, partitions, folders, notebook covers, envelopes, cardboard boxes, shipping tubes private use: diapers, changing pads, toilet pads, sanitary napkins, tampons, biodegradable urns, wrapping paper, filters for printers, toilet paper pet supplies: small animal box, dog waste bag, animal litter German utility model DE 20 2014 004 445 U1 discloses an apparatus for producing biochar and obtaining heat. The apparatus includes a motorized fuel conveyor for conveying biomass fuel in a combustor for carbonizing the extracted biomass fuel in the combustor to biochar and combusting the released volatiles for heat recovery. In addition, the apparatus comprises a biochar conveyor for discharging the biochar generated in the burner from the burner.

European Patent Application EP 0 116 414 discloses a paper-like sheet material containing at least 25% synthetic thermoplastic material and at most 75% cellulose fibers. The disadvantage here is the comparatively high content of thermoplastics.

U.S. Pat. No. 2015 027 179 (A1) discloses the use of dried digestates for further processing in a pyrolysis system to produce biochar and synthesis gas.

Malayan patent application MY 129,849 (A) discloses a process for producing a biodegradable material. In the method, a pregelatinized starch suspension is first prepared and maintained between 0° C. and 60° C. A dry or moist, homogeneous mixture containing wood fibers with an aspect ratio between 1:2 and 1:8 (width: length) is added to the suspension. The result is a homogeneous, moldable mass that can be formed in the heat to a biodegradable material.

From the German patent application DE 3.622.933 A1 a carrying case made of waste paper is known. On the outer side of the bag, a thread grid is laid, which has threads running in the longitudinal direction of the bag side surfaces. Carrying handles are attached to the upper end of the pocket side surfaces. The thread grid is a network of two intersecting threads of threads made of natural fibers. The thread grid gives the bag even when wet sufficient carrying capacity, so that it is suitable as a garbage bag. The term "thread grid" as used is intended to denote all arrangements of threads and/or fibers.

In his article »55 applications of biochar«in the Ithaca Journal, January 2012, pages 92 to 102, H.-P. Schmidt explains the advantages of biochar and gives a detailed description of the application fields of biochar.

In her article "Paper from Biochar" in the Ithaca Journal, Kathleen Draper describes the production and applications of paper from biochar. This paper illustrates the papermaking and functional properties of biochar papers.

German patent application DE 197 22 324 A1 discloses a process for the production of solid molded parts from renewable and/or organic materials. In this case, crushed or shredded cellulose-rich raw materials with 5 to 50% of a lignin-based material as solidifying agent in the form of activated by intensive wet maceration raw lignite or peat and 1 to 15% slaked lime for denaturing plant ingredients and as bonding agent between wood and activated lignite or activated peat intensive are mixed, and the mixed material is solidified to form parts after drying to a moisture content of 5 to 25% by high-pressure compression. The use of lignite or peat, however, has the disadvantage that both the starting materials and the series products can vary greatly in their material composition and their structure, which is why the particular desired performance property profile of the molded parts—if at all obtainable—is difficult and experimentally consuming to adjust and reproduce.

Object of the Invention

It is an object of the present invention to provide devices which function as moisture regulators, have a better $CO_2$ balance, constitute a $CO_2$ sink, suppress the formation of unpleasant odors and/or absorb external odors and/or poisons and/or are biocides.

A further object of the present invention is to provide apparatuses which contain or consist of biodegradable and/or compostable, fluid-resistant, in particular water-resistant, mechanically, chemically and thermally stable, weather-stable and UV-stable materials, so that they can withstand impacts, Bumps, edge stings and/or long-term chemical or thermal stress, dynamic mechanical load or static load, eg. B. stacking, not deform, burst open and/or destroyed in any other way.

In addition, the present invention has the object to provide devices that can be used in a particularly versatile manner.

Solution According to the Invention

Accordingly, VOC and pollutants absorbing and/or biocidal, gas-permeable devices have been found, containing molded parts or consisting of molded parts (F) containing materials or consisting of materials based on wood, biodegradable fibers, biodegradable films and/or separated manure containing geometrically regular and/or irregular, free and/or aggregated and/or agglomerated carbon nanoparticles, carbon microparticles and/or carbon macroparticles, the carbon being selected from the group consisting of biocarbon, biochar, charcoal, sifting residues of charcoal, wood ash, activated carbon, hard coal, animal charcoal, carbon from animal waste, pyrogenic carbon having different degrees of pyrolysis, functionalized carbons, pre-treated carbons, washed carbons and extracted carbons.

Hereinafter, the VOC and pollutants absorbing and/or biocidal, gas-permeable devices are referred to as "devices according to the invention".

In addition, numerous uses of the devices according to the invention were found, which are referred to below as "uses according to the invention".

Advantages of the Invention

In view of the prior art, it was surprising and unforeseeable for the skilled person that the object underlying the present task could be achieved by means of the devices according to the invention and the uses according to the invention.

In particular, it was surprising that the use of renewable raw materials and available resources were made possible by the devices according to the invention and that as a consequence the production of the devices according to the invention was environmentally friendly.

Surprisingly, the devices according to the invention could be recycled and likewise produced emission-free. Thus, the devices of the invention represented a $CO_2$ sink.

Particularly surprising in the devices according to the invention were the binding of pollutants and the reduction of the sick-building syndrome and the compatibility for allergy sufferers and/or for the skin. The devices according to the invention served, inter alia, as fire protection, were colorfast and/or bacteriostatic. Furthermore, they developed less dust when crushing or sawing than they normally did.

Not least, it was surprising that the devices according to the invention improved the air space regulation and/or the regulation of moisture and also that VOC and odor-forming substances were absorbed.

DETAILED DESCRIPTION

The devices according to the invention contain molded parts or consist of molded parts which contain or consist of materials. The materials are made of wood, biodegradable fibers, biodegradable films, and/or separated manure, and contain geometrically regular and/or irregular, free and/or aggregated and/or agglomerated carbon nanoparticles, carbon microparticles and/or carbon microparticles, the carbon being selected from the group consisting of biocarbon, biochar, charcoal, lumps of charcoal, lumber ashes, activated carbon, hard coal, animal charcoal, carbon from animal waste, pyrogenic carbon having different degrees of pyrolysis, functionalized carbons, pre-treated carbons, washed carbons and extracted carbons.

The molded parts that make up the devices according to the invention can have a wide variety of three-dimensional shapes. These forms depend primarily upon their use in the invention. They may therefore be, for example, plate-shaped, cuboidal, pellet-shaped, chip-shaped, spherical, cylindrical, conical, annular, tubular with or without gas-permeable walls, cloth-like, foil-shaped, grid-shaped, reticulate and/or sieve-shaped. Other three-dimensional shapes and combinations are conceivable and can be derived by the skilled person from the respective purpose of the invention.

The molded parts are permeable to gas, in particular permeable to air. The permeability can be based on the porosity of the individual molded parts in the nanometer range, micrometer range and/or millimeter range. But the molded parts may also be compact, and the permeability may result from the fact that the molded parts are present as bulk material.

Another important component of the materials that make up the molded parts is wood. Wood-based materials can consist of different types of comminuted wood, which differ in size, shape and/or arrangement. The production of, for example, plate and/or rod-shaped wood material is carried out by mixing the different wood particle shapes with natural and synthetic binders, such as adhesives, and/or an addition of other additives, wood preservatives and/or color particles. Subsequently, the mixed materials are produced to form plate and/or rod-shaped wood materials in a hot pressing and/or cold pressing, by a casting and/or bulk method.

Different types of wood-based materials are, for example:
Solid wood materials and/or materials based on solid wood
  solid wood and/or glued wood panels
    glued laminated timber and/or other board stacking constructions
    blockboard
    laminated wood and/or other solid wood elements glued together
Veneer materials
  veneered plywood (FU)
  laminated veneer lumber
  strand lumber
  bending plywood
  resin pressed wood (KP)
Wood chip materials
  flat press plate (P2)
  extruded plate
  chipboard Molded parts—Coarse Chipboard (OSB Board)
  chipboard wood (LSL)
  laminboard
  flat press plates (FP)
Wood fiber materials
  wood fiber insulation board (HFD)
  medium Hardboard (MB)
  hard fiberboard (HB and HFH)
  medium density fiberboard (MDF)
  high density fiberboard (HDF)
  multilayer boards
Composites
  wood Plastic Composites, also called wood-polymer materials
  lightweight panels
  lightweight concrete
  laminated densified wood
  rockwool cladding panels
Arboform
Cork, foamed cork, expanded cork There are many different types of wood used in different fields. The list of the following wood species is exemplary and not exhaustive. On the basis of his general knowledge, the skilled person can easily name further possible types of wood.

Conifers:
douglas fir
spruce
hemlock
pine
larch
redwood
fir
Hardwoods:
abachi
afzelia
maple
birch
pear tree
beech
oak
alder
ash
iroko
cherry tree
lime
mahogany
walnut
poplar
copper beech
robinia
teak The woods may be used in the materials alone or in combination with the biodegradable fibers, the biodegradable films and/or the separated manure.

Another essential ingredient of the materials that can be used alone or in the combinations described above are biodegradable fibers. Examples of suitable biodegradable fibers are all natural fibers, such as
  seed fibers:
    such as cotton (CO), kapok (KP), poplar fluff, acon, such as bamboo fiber, nettle, hemp fiber (HA), jute (JU), kenaf, linen (LI), Hops, ramie (RA) and hemp,
  hard fibers:
    such as pineapple, caroa, curaua, henequen, New Zealander flax, sisal (SI) and coconut (CC),
  wool and fine animal hair:
    such as wool from sheep (WO), alpaca, llama, vicuna, guanaco, angora (WA), Rabbit fur, camel hair (WK), cashmere (VVS) and mohair (WM),
  coarse animal hair:
    such as cattle hair, horsehair and goat hair,
  silk:
    such as mulberry silk (SE), tussah silk (ST) and sea silk,
  rubber fibers:
    such as rubber
  protein fibers:
    such as casein-based fibers, soy proteins, zein, albumins, collagen, glycoproteins, globulins, elastin, nucloproteins, histones, keratin, chromoproteins, protamines, fibrinogen, phosphoproteins, protamines, myosin, lipoproteins and hydrophobin and
  fibers based on starch or glucose:
    such as polylactide fibers (PLA), alginate fibers (ALG) and chitosan fibers.

Another essential constituent of the materials that can be used alone or in the combinations described above are biodegradable films such as films based on polylactic acid, polylactates, polyhydroxybutyric acids, polyhydroxy fatty acids and/or polyesters.

Another essential component of the materials that can be used alone or in the combinations described above is separated manure. Separated manure consists of solids derived from animal excrement. By inserting the separated manure into saline solution, the separated manure is disinfected and sterilized, so that germs and bacteria are killed.

Yet another essential component of the materials from which the molded parts are constructed is carbon, also pyrogenic, naturally occurring and biologically produced carbon, which is present as carbon nanoparticles, carbon microparticles and/or carbon macroparticles.

The carbon nanoparticles have an average particle size of 1 nm to <1000 nm, the carbon microparticles have an average particle size of ≥1000 nm to <1000 μm and the carbon nanoparticles an average particle size of ≥1000 μm.

In the context of the present invention, the term "nanoparticle" denotes particles having an average particle size of from 1 nm to <1000 nm.

Furthermore, the term "microparticle" refers to particles having an average particle size of 1 μm to <1000 μm.

The term "macroparticle" refers to particles with a mean particle size of ≥1000 μm.

The carbon is introduced in the form of charcoal and/or sieve residues and/or wood ash, activated carbon, hard coal, animal charcoal, carbon from animal waste, pyrogenic carbon having different degrees of pyrolysis, functionalized carbons, pre-treated carbons, washed carbons, carbon with different degrees of charring and extracted carbon and/or is obtained by a pyrolysis process in a mobile or stationary pyrolysis plant from predominantly lignin-rich, organic materials such as wood, plant stems, fruit pits, nut shells and/or bones.

Preferably, the pyrolysis process is operated under oxygen exclusion at about 100 to 1000° C. However, the person skilled in the art understands how to adapt the corresponding pyrolysis conditions to the respective conditions, such as the type of pyrolysis plant, the ambient pressure and/or the amount of the type and nature of the pyrolysis product.

To produce the carbon, in a preferred embodiment, the pyrolysis material can be cut and/or comminuted before and/or after and/or pressed into compacts. These have the advantage that the pyrolysis process is better controllable and a more homogeneous pyrolysis product is delivered, which favors the subsequent processing. Otherwise, to obtain carbon, the pyrolysis material would have to be first separated according to its nature, for example after bark, grass, wood or bone, before it is fed to the respective pyrolysis process.

In addition to the carbon produced in the pyrolysis, other usable products are adopted, such as oils, wood tar and/or gases that can be used, for example, for electricity, heat, and/or refrigeration and also as raw materials. As a result, these by-products are applicable for a meaningful use, for example energy production, and recoverable and usable in the context of the invention for the packaging material.

The skilled person knows in addition to pyrolysis also other processes for the production of carbon. As an example, the hydrothermal carbonization method may be mentioned.

The carbon produced by various methods has intramolecular carbon structures, that can be e.g. influenced by the pyrolysis. Thereby, the properties of the carbon used for the method according to the invention can be adapted in view of a high nutrient and water storage capacity.

The carbon nanoparticles, carbon microparticles and/or carbon macroparticles can have a wide variety of morphologies and geometric shapes, so that they can be perfectly adapted to the other constituents of the material.

Thus, they can be compact, and have at least one cavity and/or a core-shell structure. In addition, these cavities can also be different in size. One can also use different geometric shapes, such as spheres, ellipsoids, cubes, cuboids, pyramids, cones, cylinders, rhombuses, dodecahedra, truncated dodecahedron, meander, fractal, icosahedron, truncated icosahedron, dumbbells, tori, platelets, or needles with a circular, oval elliptical, square, triangular, quadrangular, pentagonal, hexagonal, heptagonal, octagonal, or star-shaped (tri, tetra, pentagonal, or polygonal) outline. If necessary, existing edges and corners can be rounded. It is also possible for two or more carbon nanoparticles, carbon microparticles and/or carbon macroparticles of different morphology and/or geometric form to be assembled together. For example, but not by way of limitation, spherical carbon nanoparticles, carbon microparticles, and/or carbon macroparticles may have pointed outgrowths in the form of cones. Furthermore, their surface may have depressions such that the carbon nanoparticles, carbon microparticles and/or carbon macroparticles have a strawberry or raspberry morphology. Last but not least, the dumbbell, tori, needles or plates can be bent in at least one direction of the room. They can be freely selectable in any form.

The particle size distribution of the carbon nanoparticles, carbon microparticles and/or carbon macroparticles can vary very widely, be monodisperse, oligodisperse and/or polydisperse and can therefore be perfectly adapted to the respective intended use of the process according to the invention.

The amounts of carbon used can vary very widely and depend mainly on the size and thickness of the respective materials according to the invention. Preferably, the amounts used are from 0.1 to 95 wt.-%, preferably 0.5 to 75 wt.-% and in particular 1 to 50 wt.-%, each based on the total amount of material.

The carbon nanoparticles, carbon microparticles and/or carbon macroparticles may be surrounded by a shell and/or carry at least one functional group. In this case, the material of the shells may carry the functional group or else the functional groups may be present directly on the surface of the carbon nanoparticles, carbon microparticles and/or carbon macroparticles.

Furthermore, the carbon may be surface modified, crushed, crushed and dried, dried, dried and moistened, and crushed and partially dried, steamed, cooked and/or treated with boiler pressure.

The sheaths and/or the functional groups may be bonded to the surface of the carbon nanoparticles, carbon microparticles and/or carbon macroparticles via covalent and/or ionic bonds and/or electrostatic and/or van der Waals forces and/or mechanical molecular interweaving.

The bond between the surfaces of the carbon nanoparticles, carbon microparticles and/or carbon macroparticles and the shell and/or functionalized groups can be permanent or reversible, i.e. solvable.

The following are examples of suitable functional groups and materials for the shells of the carbon nanoparticles, carbon microparticles and/or carbon macroparticles to be used according to the invention. The person skilled in the art can select the functional groups and materials which are particularly suitable for the particular case on the basis of the property profiles known to him.

Common and Known Functional Groups:

Fluorine, chlorine, bromine and iodine atoms; Hydroxyl, thiol, ether, thioether, amino, peroxide, aldehyde, acetate, carboxyl peroxycarboxyl, ester, amide, hydrazide and urethane groups; Imide, hydrazone and hydroxime, amide, hxdroxamic acid groups; Groups derived from formamidine, formamidoxime, formamidrazone, formhydrazidine, formhydrazidoxime, formamidrazone, formhydroxamoxime and formoxamidrazone; Nitrile, isocyanate, thiocyanate, isothiocyanate, isonitrile, lactide, lactone, lactam, oxime, nitroso, nitro, azo, azoxy, hydrazine, azine, carbodiimide, azide, Azane, sulfen, sulfenamide, sulfonamide, thioaldehyde, thioketone, thioacetal, thiocarboxylic acid, sulfonium, sulfur halide, sulfoxide, sulfone, sulfimine, sulfoximine, sultone, sultam, sulfone, Silane, siloxane phosphine, phosphine oxide, phosphonium, phosphoric acid, phosphorous acid, phosphonic acid, phosphate, phosphinate and phosphonate groups.

Preferably, the carbon nanoparticles, carbon microparticles and/or carbon macroparticles are also functionalized with lignin.

The carbon nanoparticles, carbon microparticles and/or carbon macroparticles can also contain oxidative functionalizations e.g. by plasma treatment.

The carbon nanoparticles, carbon microparticles and/or carbon macroparticles described above can be incorporated into the materials in a wide variety of ways.

The following are examples of incorporation of carbon nanoparticles, carbon microparticles and/or carbon macroparticles into the materials in the form of additives and auxiliaries, fillers and adhesives. The person skilled in the art can select the functional groups and materials which are particularly suitable for the particular case on the basis of the property profiles known to him.

Usual and Known Functional and/or Non-Functional Additives:

Examples of suitable additives are low-boiling organic solvents and high-boiling organic solvents ("long solvents"), water, UV absorbers, light stabilizers, free-radical scavengers, defoamers, emulsifiers, wetting and dispersing agents and tensides, adhesion promoters, leveling agents, film-forming auxiliaries, rheology-controlling additives (Thickeners), flame retardants, desiccants, drying agents, skin preventatives, corrosion inhibitors, waxes, matting agents or reinforcing fibers.

Examples of suitable low-boiling organic solvents and high-boiling organic solvents ("long solvents") are ketones such as methyl ethyl ketone, methyl isoamy ketone or methyl isobutyl ketone, esters such as ethyl acetate, butyl acetate, ethyl ethoxypropionate, methoxypropyl acetate or butyl glycol acetate, ethers such as dibutyl ether or ethylene glycol, diethylene glycol, propylene glycol, dipropylene glycol, Butylenglykol- or Dibutylenglykoldimethyl-, -dietyl- or -dibutylether, N-methylpyrrolidone or xylenes or mixtures of aromatic and/or aliphatic hydrocarbons such as solvent naphtha®, gasoline 135/180, Dipentene or Solvesso®.

Examples of suitable emulsifiers, wetting and dispersing agents or surfactants are the customary and known anionic, cationic, nonionic and zwitterionic wetting agents, as described in detail, for example, in Römpp Online, April 2014, Georg Thieme Verlag, "wetting agents".

An example of a suitable coupling agent is tricyclodecanedimethanol.

Examples of suitable film-forming auxiliaries are cellulose derivatives such as cellulose acetobutyrate (CAB).

Examples of suitable rheology-spreading additives are the crosslinked polymeric microparticles known from the patents WO 94/22968, EP 0 276 501 A1, EP 0 249 201 A1 or WO 97/12945, as disclosed, for example, in EP 0 008 127 A1; inorganic phyllosilicates such as aluminum-magnesium silicates, sodium magnesium and sodium magnesium fluorine lithium phyllosilicates of the montmorillonite type; Silicas such as aerosils; or synthetic polymers having ionic and/or associative groups such as polyvinyl alcohol, poly (meth) acrylamide, poly (meth) acrylic acid, polyvinylpyrrolidone, styrene-maleic anhydride or ethylene-maleic anhydride copolymers and their derivatives or hydrophobically modified, ethoxylated urethanes or polyacrylates.

An example of a suitable matting agent is magnesium stearate.

The carbon nanoparticles, carbon microparticles and/or carbon macroparticles may also undergo functionalizations and/or impregnations with anionic surfactants and/or polyanionic compounds and/or starch and/or starch-like compound and/or zein. Furthermore, they may be laden with humic substances, superabsorbents, concrete and/or montmorillonite.

Common and Known Fillers:

Examples of suitable fillers are those based on phyllosilicates, titanium dioxide, and also black titanium dioxide, sand, silicon oxide, aluminum oxide or zirconium oxide; in addition, reference is made to the Rompp Lexikon Lacke and printing inks, Georg Thieme Verlag, Stuttgart, 1998, pages 250 to 252.

Common and Known Adhesives:

Examples of suitable adhesives are biopolymers, polysaccharides, chemically curing adhesives, polymerization adhesives, cyanoacrylate adhesives (superglues), methylmethacrylic adhesives, anaerobic curing adhesives, unsaturated polyesters (UP resins), radiation curing adhesives, polycondensation adhesives, phenol-formaldehyde resin adhesives, silicone adhesives. Silane cross-linked polymer adhesives polymide adhesives, polysulfide adhesives, polyaddition adhesives, epoxy resin adhesives, polyurethane adhesives, silicone polyisocyanate adhesives, physical bonding adhesives, solvent borne adhesives Lime and slaked lime and adhesives based thereon, physically binding adhesives, urea-formaldehyde (UF), melamine-urea-formaldehyde (MUF), polymers isocyanates (PMDI), polyvinyl acetate (PVAC), kaurite, Ka his and lime, flour and/or starch.

Common and Known Flame Retardants:

polybrominated diphenyl ethers (pentaBDE, octaBDE, decaBDE), TBBPA, HBCD, polybombated biphenyls (PBB), chloroparaffins, mirex, halogenated flame retardants, melamine, urea, TCEP (tris (chloroethyl) phosphate), TCPP (tris (chloropropyl)) phosphate), TDCPP (Tris (dichloroisopropyl) phosphates), TPP (triphenyl phosphate), TEHP (tris-(2-ethylhexyl) phosphate), TKP (tricresyl phosphate), ITP ("isopropylated triphenyl phosphate") mono-, bis- and tris (isopropylphenyl) phosphates of different isopropylation grade, RDP (resorcinol bis (diphenyl phosphate)), BDP (bisphenol A bis (diphenyl phosphate)), aluminum hydroxide [Al(OH)3], magnesium hydroxide [Mg (OH)2, MDH, "magnesium dihydrate"], ammonium sulfate [(NH4)2SO4] and -phosphate [(NH4) 3PO4], red phosphorus, antimony trioxide (Sb2O3), antimony pentoxide (Sb2O5), zinc borate, lime extender [Ca (OH)2].

The above additives, fillers and adhesives can be treated with carbon nanoparticles, carbon microparticles and/or carbon macroparticles are enriched together to bind them in themselves. The materials, additives, fillers and/or adhesives listed above are exemplary only and not fully listed. The person skilled in the art can easily, on the basis of his general knowledge, name further possible materials, additives, fillers and/or adhesives.

Plastics consist for the most part of organic monomers which react with each other by various methods, such as polyaddition, polymerization and/or polycondensation and thereby form macromolecular polymer. The plastics differ in their properties between elastomers, these are elastically deformable and linearly linked in a wide temperature range, plastomers, also called thermoplastics, these are repeatedly plastically deformable, temperature-dependent and branched with semi-crystalline regions, and duromers, also called thermosets, these are in the intermediate stage plastically deformable, after hardening no longer deformable and strongly cross-linked.

The list below lists some possible plastics. The list is exemplary and not exhaustive. The person skilled in the art, on the basis of his general knowledge, can easily name further possible plastics.

Common and Known Plastics:
phenol formaldehyde (PF)
urea formaldehyde (UF)
unsaturated polyester (UP)
acrylic nitrite (ABS)
cellulose acetate (CA)

polyamide (PA)
polycarbonate (PC)
polyethylene (PE)
polyisobutylene (PIB)
polymethylmethacrylate (PMMA)
polypropylene (PP)
polystyrene (PS)
PS rigid foam (PS-E)
polytetrafluoroethylene (PTFE)
polyurethane (PUR)
polyvinyl chloride (PVC)
epoxy resin (EP)
melamine formaldehyde (MF)

According to the standard DIN EN 26927, sealants are divided into plastic and/or elastic sealants. Plastic sealants are sprayable. They do not completely harden and retain the plastic behavior. Furthermore, the resilience is low and the use of these sealants only partially possible. Elastic sealants are also sprayable. After crosslinking, they behave like rubber and the resilience is good. Furthermore, deformations, as long as the maximum elongation and/or elongation is not exceeded, form again.

In the list below types of sealants are exemplary and not fully listed. One of ordinary skill in the art can readily identify other possible types of sealants.

Common and Known Types of Sealants:
linseed oil
butyl
polyisobutylene
acrylates, solvent-based and/or dispersion
polyurethane, one-component and/or two-component
polysulfides, one-component and/or two-component
polysiloxanes Furthermore, the materials according to the invention can be modified with other materials. Examples of materials are damping materials, insulating materials, films, in particular aluminum foil, and/or other materials.

Examples of suitable damping materials and/or insulating materials are listed in the following list. These are only examples and not fully listed. On the basis of his general knowledge, the person skilled in the art can easily name further possible damping materials and/or insulating materials.

Damping materials and/or insulations
expanded polystyrene (ESP)
extruded polystyrene (XPS)
polyurethane rigid foam (PU)
polyurethane in situ foam (PU)
rock wool
glass wool
foam glass
expanded pearlite
cork sheets/-granulated
expanded cork
cellulose fluff/-mats
sheep's wool
coconut mats
reed
expanded cement In addition, the active ingredients may be treated with dry medium In, such as, for example, superabsorbers, phyllosilicates, nanoclay, kieselguhr and/or zeolites. The list below lists the various desiccants as examples. The person skilled in the art, on the basis of his general knowledge, can easily name further possible desiccants.

Usual and Known Phyllosilicates:

The elemental composition and structure of the layered silicate micro- and/or nanoparticles can also vary widely.

For example, the classification of silicates into the following structures is known:
island silicates
group silicates
ring silicates
chain and tape silicates
transition structures between chain and layer silicates
phyllosilicates
framework silicates Phyllosilicates are silicates whose silicates consist of layers of corner-sharing SiO4 tetrahedra. These layers and/or bilayers are not further linked to one another. The technically important and in sedimentary rocks widespread clay minerals are also phyllosilicates. The layered structure of these minerals determines the shape and properties of the crystals. They are usually tabular to leafy with good to perfect cleavage parallel to the layers. The number of rings that make up the silicate layers often determines the symmetry and shape of the crystals. Between the layers can become water molecules, large cations and/or lipids. Phyllosilicates are often swellable and with their cation exchange capacity important for the fertility of soils.

For example, in the table below, the visual silicates are listed and not exhaustive. The person skilled in the art can readily cite further phyllosilicates which are particularly suitable for the individual case.

TABLE 1

Sum formulas of suitable phyllosilicates[a)]

| Nr. | Type | Empirical formula |
|---|---|---|
| 1 | martinite | $(Na,Ca)_{11}Ca_4(Si,S,B)_{14}B_2O_{40}F_2 \cdot (H_2O)$ |
| 2 | apophyllite-(NaF) | $NaCa_4Si_8O_{20}F \cdot 8H_2O$ |
| 3 | apophyllite-(KF) | $(K,Na)Ca_4Si_8O_{20}(F,OH) \cdot 8H_2O$ |
| 4 | apophyllite-(KOH) | $KCa_4Si_8O_{20}(OH,F) \cdot 8H_2O$ |
| 5 | cuprorivaite | $CaCuSi_4O_{10}$ |
| 6 | wesselsite | $(Sr,Ba)Cu[Si_4O_{10}]$ |
| 7 | effenbergerite | $BaCu[Si_4O_{10}]$ |
| 8 | gillespite | $BaFe^{2+}Si_4O_{10}$ |
| 9 | sanbornite | $BaSi_2O_5$ |
| 10 | bigcreekite | $BaSi_2O_5 \cdot 4H_2O$ |
| 11 | davanite | $K_2TiSi_6O_{15}$ |
| 12 | dalyite | $K_2ZrSi_6O_{15}$ |
| 13 | fenaksite | $KNaFe^{2+}Si_4O_{10}$ |
| 14 | manaksite | $KNaMn^{2+}[Si_4O_{10}]$ |
| 15 | ershovite | $K_3Na_4(Fe,Mn,Ti)_2[Si_8O_{20}(OH)_4] \cdot 4H_2O$ |
| 16 | paraershovite | $Na_3K_3Fe^{3+}{}_2Si_8O_{20}(OH)_4 \cdot 4H_2O$ |

TABLE 1-continued

Sum formulas of suitable phyllosilicates[a)]

| Nr. | Type | Empirical formula |
|---|---|---|
| 17 | natrosilite | $Na_2Si_2O_5$ |
| 18 | kanemite | $NaSi_2O_5 \cdot 3H_2O$ |
| 19 | revdite | $Na_{16}Si_{16}O_{27}(OH)_{26} \cdot 28H_2O$ |
| 20 | latiumite | $(Ca,K)_4(Si,Al)_5O_{11}(SO_4,CO_3)$ |
| 21 | tuscanite | $K(Ca,Na)_6(Si,Al)_{10}O_{22}(SO_4,CO_3,(OH)_2) \cdot H_2O$ |
| 22 | carletonite | $KNa_4Ca_4Si_8O_{18}(CO_3)_4(OH,F) \cdot H_2O$ |
| 23 | pyrophyllite | $Al_2Si_4O_{10}(OH)_2$ |
| 24 | ferripyrophyllite | $Fe^{3+}Si_2O_5(OH)$ |
| 25 | macaulayite | $(Fe^{3+},Al)_{24}Si_4O_{43}(OH)_2$ |
| 26 | talc | $Mg_3Si_4O_{10}(OH)_2$ |
| 27 | minnesotaite | $Fe^{2+}_3Si_4O_{10}(OH)_2$ |
| 28 | willemseite | $(Ni,Mg)_3Si_4O_{10}(OH)_2$ |
| 29 | pimelite | $Ni_3Si_4O_{10}(OH)_2 \cdot 4H_2O$ |
| 30 | kegelite | $Pb_4Al_2Si_4O_{10}(SO_4)(CO_3)_2(OH)_4$ |
| 31 | aluminoseladonite | $K(Mg,Fe^{2+})Al[(OH)_2|Si_4O_{10}]$ |
| 32 | ferroaluminoseladonite | $K(Fe^{2+},Mg)(Al,Fe^{3+})[(OH)_2|Si_4O_{10}]$ |
| 33 | seladonite | $K(Mg,Fe^{2+})(Fe^{3+},Al)Si_4O_{10}(OH)_2$ |
| 34 | chromseladonite | $KMgCr[(OH)_2|Si_4O_{10}]$ |
| 35 | ferroseladonite | $K(Fe^{2+},Mg)(Fe^{3+},Al)[(OH)_2|Si_4O_{10}]$ |
| 36 | paragonite | $NaAl_2(Si_3Al)O_{10}(OH)_2$ |
| 37 | boromuscovite | $KAl_2(Si_3B)O_{10}(OH,F)_2$ |
| 38 | muscovite | $KAl_2(Si_3Al)O_{10}(OH,F)_2$ |
| 39 | chromphyllite | $K(Cr,Al)_2[(OH,F)_2|AlSi_3O_{10}]$ |
| 40 | roscoelite | $K(V,Al,Mg)_2AlSi_3O_{10}(OH)_2$ |
| 41 | ganterite | $(Ba,Na,K)(Al,Mg)_2[(OH,F)_2|(Al,Si)Si_2O_{10}]$ |
| 42 | tobelite | $(NH_4,K)Al_2(Si_3Al)O_{10}(OH)_2$ |
| 43 | nanpingite | $CsAl_2(Si,Al)_4O_{10}(OH,F)_2$ |
| 44 | polylithionite | $KLi_2AlSi_4O_{10}(F,OH)_2$ |
| 45 | tainiolite | $KLiMg_2Si_4O_{10}F_2$ |
| 46 | norrishite | $KLiMn^{3+}_2Si_4O_{12}$ |
| 47 | shirokshinite | $KNaMg_2[F_2|Si_4O_{10}]$ |
| 48 | montdorite | $KMn_{0.5}^{2+}Fe_{1.5}^{2+}Mg_{0.5}[F_2|Si_4O_{10}]$ |
| 49 | trilithionite | $KLi_{1.5}Al_{1.5}[F_2|AlSi_3O_{10}]$ |
| 50 | masutomilite | $K(Li,Al,Mn^{2+})_3(Si,Al)_4O_{10}(F,OH)_2$ |
| 51 | aspidolite-1M | $NaMg_3(AlSi_3)O_{10}(OH)_2$ |
| 52 | fluorophlogopite | $KMg_3(AlSi_3)O_{10}F_2$ |
| 53 | phlogopite | $KMg_3(Si_3Al)O_{10}(F,OH)_2$ |
| 54 | tetraferriphlogopite | $KMg_3[(F,OH)_2|(Al,Fe^{3+})Si_3O_{10}]$ |
| 55 | hendricksite | $K(Zn,Mn)_3Si_3AlO_{10}(OH)_2$ |
| 56 | shirozulite | $K(Mn^{2+},Mg)_3[(OH)_2|AlSi_3O_{10}]$ |
| 57 | fluorannite | $KFe_3^{2+}[(F,OH)_2|AlSi_3O_{10}]$ |
| 58 | annite | $KFe^{2+}_3(Si_3Al)O_{10}(OH,F)_2$ |
| 59 | tetraferriannite | $KFe^{2+}_3(Si_3Fe^{3+})O_{10}(OH)_2$ |
| 60 | ephesite | $NaLiAl_2(Al_2Si_2)O_{10}(OH)_2$ |
| 61 | preiswerkite | $NaMg_2Al_3Si_2O_{10}(OH)_2$ |
| 62 | eastonite | $KMg_2Al[(OH)_2|Al_2Si_2O_{10}]$ |
| 63 | siderophyllite | $KFe_2^{2+}Al(Al_2Si_2)O_{10}(F,OH)_2$ |
| 64 | anandite | $(Ba,K)(Fe^{2+},Mg)_3(Si,Al,Fe)_4O_{10}(S,OH)_2$ |
| 65 | bityite | $CaLiAl_2(AlBeSi_2)O_{10}(OH)_2$ |
| 66 | oxykinoshitalite | $(Ba,K)(Mg,Fe^{2+},Ti^{4+})_3(Si,Al)_4O_{10}O_2$ |
| 67 | kinoshitalite | $(Ba,K)(Mg,Mn,Al)_3Si_2Al_2O_{10}(OH)_2$ |
| 68 | ferrokinoshitalite | $Ba(Fe^{2+},Mg)_3[(OH,F)_2|Al_2Si_2O_{10}]$ |
| 69 | margarite | $CaAl_2(Al_2Si_2)O_{10}(OH)_2$ |
| 70 | chernykhite | $BaV_2(Si_2Al_2)O_{10}(OH)_2$ |
| 71 | clintonite | $Ca(Mg,Al)_3(Al_3Si)O_{10}(OH)_2$ |
| 72 | wonesite | $(Na,K,)(Mg,Fe,Al)_6(Si,Al)_8O_{20}(OH,F)_4$ |
| 73 | brammallite | $(Na,H_3O)(Al,Mg,Fe)_2(Si,Al)_4O_{10}[(OH)_2,H_2O]$ |
| 74 | illite | $(K,H_3O)Al_2(Si_3Al)O_{10}(H_2O,OH)_2$ |
| 75 | glauconite | $(K,Na)(Fe^{3+},Al,Mg)_2(Si,Al)_4O_{10}(OH)_2$ |
| 76 | agrellite | $NaCa_2Si_4O_{10}F$ |
| 77 | glagolevite | $NaMg_6[(OH,O)_8|AlSi_3O_{10}] \cdot H_2O$ |
| 78 | erlianite | $Fe^{2+}_4Fe_{3+2}Si_6O_{15}(OH)_8$ |
| 79 | bannisterite | $(Ca,K,Na)(Mn^{2+},Fe^{2+},Mg,Zn)_{10}(Si,Al)_{16}O_{38}(OH)_8 \cdot nH_2O$ |
| 80 | bariumbannisterite | $(K,H_3O)(Ba,Ca)(Mn^{2+},Fe^{2+},Mg)_{21}(Si,Al)_{32}O_{80}(O,OH)_{16} \cdot 4\text{-}12H_2O$ |
| 81 | lennilenapeite | $K_{6\text{-}7}(Mg,Mn,Fe^{2+},Fe^{3+},Zn)_{48}(Si,Al)_{72}(O,OH)_{216} \cdot 16H_2O$ |
| 82 | stilpnomelane | $K(Fe^{2+},Mg,Fe^{3+},Al)_8(Si,Al)_{12}(O,OH)_{27} \cdot 2H_2O$ |
| 83 | franklinphilite | $(K,Na)_{1-x}(Mn^{2+},Mg,Zn,Fe^{3+})_8(Si,Al)_{12}(O,OH)_{36} \cdot nH_2O$ |
| 84 | parsettensite | $(K,Na,Ca)_{7.5}(Mn,Mg)_{49}Si_{72}O_{168}(OH)_{50} \cdot nH_2O$ |
| 85 | middendorfite | $K_3Na_2Mn_5Si_{12}(O,OH)_{36} \cdot 2H_2O$ |
| 86 | eggletonite | $(Na,K,Ca)_2(Mn,Fe)_8(Si,Al)_{12}O_{29}(OH)_7 \cdot 11H_2O$ |
| 87 | ganophyllite | $(K,Na)_xMn^{2+}_6(Si,Al)_{10}O_{24}(OH)_4 \cdot nH_2O$ {x = 1-2}{n = 7-11} |
| 88 | tamaite | $(Ca,K,Ba,Na)_{3\text{-}4}Mn^{2+}_{24}[(OH)_{12}|\{(Si,Al)_4(O,OH)_{10}\}_{10}] \cdot 21H_2O$ |
| 89 | ekmanite | $(Fe^{2+},Mg,Mn,Fe^{3+})_3(Si,Al)_4O_{10}(OH)_2 \cdot 2H_2O$ |
| 90 | lunijianlaite | $Li_{0.7}Al_{6.2}(Si_7AlO_{20})(OH,O)_{10}$ |
| 91 | saliotite | $Na_{0.5}Li_{0.5}Al_3[(OH)_5|AlSi_3O_{10}]$ |
| 92 | kulkeite | $Na_{0.35}Mg_8Al(AlSi_7)O_{20}(OH)_{10}$ |

TABLE 1-continued

Sum formulas of suitable phyllosilicates[a]

| Nr. | Type | Empirical formula |
|---|---|---|
| 93 | aliettite | $Ca_{0.2}Mg_6(Si,Al)_8O_{20}(OH)_4 \cdot 4H_2O$ |
| 94 | rectorite | $(Na,Ca)Al_4(Si,Al)_8O_{20}(OH)_4 \cdot 2H_2O$ |
| 95 | tarasovite | $(Na,K,H_3O,Ca)_2Al_4[(OH)_2|(Si,Al)_4O_{10}]_2 \cdot H_2O$ |
| 96 | tosudite | $Na_{0.5}(Al,Mg)_6(Si,Al)_8O_{18}(OH)_{12} \cdot 5H_2O$ |
| 97 | corrensite | $(Ca,Na,K)(Mg,Fe,Al)_9(Si,Al)_8O_{20}(OH)_{10} \cdot nH_2O$ |
| 98 | brinrobertsite | $(Na,K,Ca)_{0.3}(Al,Fe,Mg)_4(Si,Al)_8O_{20}(OH)_4 \cdot 3.5H_2O$ |
| 99 | montmorillonite | $(Na,Ca)_{0.3}(Al,Mg)_2Si_4O_{10}(OH)_2 \cdot nH_2O$ |
| 100 | beidellite | $(Na,Ca_{0.5})_{0.3}Al_2(Si,Al)_4O_{10}(OH)_2 \cdot 4H_2O$ |
| 101 | nontronite | $Na_{0.3}Fe_2^{3+}(Si,Al)_4O_{10}(OH)_2 \cdot 4H_2O$ |
| 102 | volkonskoite | $Ca_{0.3}(Cr^{3+},Mg,Fe^{3+})_2(Si,Al)_4O_{10}(OH)_2 \cdot 4H_2O$ |
| 103 | swinefordite | $(Ca,Na)_{0.3}(Al,Li,Mg)_2(Si,Al)_4O_{10}(OH,F)_2 \cdot 2H_2O$ |
| 104 | yakhontovite | $(Ca,Na,K)_{0.3}(CuFe^{2+}Mg)_2Si_4O_{10}(OH)_2 \cdot 3H_2O$ |
| 105 | hectorite | $Na_{0.3}(Mg,Li)_3Si_4O_{10}(F,OH)_2$ |
| 106 | saponite | $(Ca|_2,Na)_{0.3}(Mg,Fe^{2+})_3(Si,Al)_4O_{10}(OH)_2 \cdot 4H_2O$ |
| 107 | ferrosaponite | $Ca_{0.3}(Fe^{2+},Mg,Fe^{3+})_3[(OH)_2|(Si,Al)Si_3O_{10}] \cdot 4H_2O$ |
| 108 | spadaite | $MgSiO_2(OH)_2 \cdot H_2O$ |
| 109 | stevensite | $(Ca|_2)_{0.3}Mg_3Si_4O_{10}(OH)_2$ |
| 110 | sauconite | $Na_{0.3}Zn_3(Si,Al)_4O_{10}(OH)_2 \cdot 4H_2O$ |
| 111 | zinksilite | $Zn_3Si_4O_{10}(OH)_2 \cdot 4H_2O$ |
| 112 | vermiculite | $Mg_{0.7}(Mg,Fe,Al)_6(Si,Al)_8O_{20}(OH)_4 \cdot 8H_2O$ |
| 113 | rilandite | $(Cr^{3+},Al)_6SiO_{11} \cdot 5H_2O$ |
| 114 | donbassite | $Al_{2.3}[(OH)_8|AlSi_3O_{10}]$ |
| 115 | sudoite | $Mg_2Al_3(Si_3Al)O_{10}(OH)_8$ |
| 116 | clinochlore | $(Mg,Fe^{2+})_5Al(Si_3Al)P_{10}(OH)_8$ |
| 117 | chamosite | $(Fe^{2+},Mg,Fe^{3+})_5Al(Si_3Al)O_{10}(OH,O)_8$ |
| 118 | orthochamosite | $(Fe^{2+},Mg,Fe^{3+})_5Al(Si_3Al)O_{10}(OH,O)_8$ |
| 119 | baileychlore | $(Zn,Fe^{2+},Al,Mg)_6(Si,Al)_4O_{10}(OH)_8$ |
| 120 | pennantite | $Mn^{2+}{}_5Al(Si_3Al)O_{10}(OH)_8$ |
| 121 | nimite | $(Ni,Mg,Fe^{2+})_5Al(Si_3Al)O_{10}(OH)_8$ |
| 122 | gonyerite | $Mn^{2+}{}_5Fe^{3+}(Si_3Fe^{3+}O_{10})(OH)_8$ |
| 123 | cookeite | $LiAl_4(Si_3Al)O_{10}(OH)_8$ |
| 124 | borocookeite | $Li_{1-1.5}Al_{4-3.5}[(OH,F)_8|(B,Al)Si_3O_{10}]$ |
| 125 | manandonite | $Li_2Al_4[(Si_2AlB)O_{10}](OH)_8$ |
| 126 | franklinfurnaceite | $Ca_2(Fe^{3+}Al)Mn_{3+}Mn_3^{2+}Zn_2Si_2O_{10}(OH)_8$ |
| 127 | chromian clinochlore (var. of chlinochlore) | $Mg_5(Al,Cr)_2Si_3O_{10}(OH)_8$ |
| 128 | niksergievite | $(Ba,Ca)_2Al_3[(OH)_6|CO_3|(Si,Al)_4O_{10}] \cdot 0.2H_2O$ |
| 129 | surite | $Pb_2Ca(Al,Mg)_2(Si,Al)_4O_{10}(OH)_2(CO_3,OH)_3 \cdot 0.5H_2O$ |
| 130 | ferrisurite | $(Pb,Ca)_{2-3}(Fe^{3+},Al)_2[(OH,F)_{2.5-3}|(CO_3)_{1.5-2}|Si_4O_{10}] \cdot 0.5H_2O$ |
| 131 | kaolinite | $Al_2Si_2O_5(OH)_4$ |
| 132 | dickite | $Al_2Si_2O_5(OH)_4$ |
| 133 | halloysite-7Å | $Al_2Si_2O_5(OH)_4$ |
| 134 | sturtite | $Fe^{3+}(Mn^{2+},Ca,Mg)Si_4O_{10}(OH)_3 \cdot 10H_2O$ |
| 135 | allophane | $Al_2O_3 \cdot (SiO_2)_{1.3-2} \cdot (H_2O)_{2.5-3}$ |
| 136 | imogolite | $Al_2SiO_3(OH)_4$ |
| 137 | odinite | $(Fe^{3+},Mg,Al,Fe^{2+},Ti,Mn)_{2.4}(Si_{1.8}Al_{0.2})O_5(OH)_4$ |
| 138 | hisingerite | $Fe_2^{3+}Si_2O_5(OH)_4 \cdot 2H_2O$ |
| 139 | neotokite | $(Mn,Fe^{2+})SiO_3 \cdot H_2O$ |
| 140 | chrysotile | $Mg_3Si_2O_5(OH)_4$ |
| 141 | clinochrysotile | $Mg_3Si_2O_5(OH)_4$ |
| 142 | maufite | $(Mg,Ni)Al_4Si_3O_{13} \cdot 4H_2O$ |
| 143 | orthochrysotile | $Mg_3Si_2O_5(OH)_4$ |
| 144 | parachrysotile | $Mg_3Si_2O_5(OH)_4$ |
| 145 | antigorite | $(Mg,Fe^{2+})_3Si_2O_5(OH)_4$ |
| 146 | lizardite | $Mg_3Si_2O_5(OH)_4$ |
| 147 | karyopilite | $Mn^{2+}{}_3Si_2O_5(OH)_4$ |
| 148 | greenalite | $(Fe^{2+},Fe^{3+})_{2-3}Si_2O_5(OH)_4$ |
| 149 | berthierine | $(Fe^{2+},Fe^{3+},Al)_3(Si,Al)_2O_5(OH)_4$ |
| 150 | fraipontite | $(Zn,Al)_3(Si,Al)_2O_5(OH)_4$ |
| 151 | zinalsite | $Zn_7Al_4(SiO_4)_6(OH)_2 \cdot 9H_2O$ |
| 152 | dozyite | $Mg_7(Al,Fe^{3+},Cr)_2[(OH)_{12}|Al_2Si_4O_{15}]$ |
| 153 | amesite | $Mg_2Al(SiAl)O_5(OH)_4$ |
| 154 | kellyite | $(Mn^{2+},Mg,Al)_3(Si,Al)_2O_5(OH)_4$ |
| 155 | cronstedtite | $Fe_2^{2+}Fe^{3+}(SiFe^{3+})O_5(OH)_4$ |
| 156 | karpinskite | $(Mg,Ni)_2Si_2O_5(OH)_2$ |
| 157 | nepouite | $(Ni,Mg)_3Si_2O_5(OH)_4$ |
| 158 | pecoraite | $Ni_3Si_2O_5(OH)_4$ |
| 159 | brindleyite | $(Ni,Mg,Fe^{2+})_2Al(SiAl)O_5(OH)_4$ |
| 160 | carlosturanite | $(Mg,Fe^{2+},Ti)_{21}(Si,Al)_{12}O_{28}(OH)_{34} \cdot H_2O$ |
| 161 | pyrosmalithe-(Fe) | $(Fe^{2+},Mn)_8Si_6O_{15}(Cl,OH)_{10}$ |
| 162 | pyrosmalithe-(Mn) | $(Mn,Fe^{2+})_8Si_6O_{15}(OH,Cl)_{10}$ |
| 163 | brokenhillite | $(Mn,Fe)_8Si_6O_{15}(OH,Cl)_{10}$ |
| 164 | nelenite | $(Mn,Fe^{2+})_{16}Si_{12}As^{3+}{}_3O_{36}(OH)_{17}$ |
| 165 | schallerite | $(Mn^{2+},Fe_{2+})_{16}Si_{12}As^{3+}{}_3O_{36}(OH)_{17}$ |
| 166 | friedelite | $Mn^{2+}{}_8Si_6O_{15}(OH,Cl)_{10}$ |
| 167 | mcgillite | $Mn^{2+}{}_8Si_6O_{15}(OH)_8Cl_2$ |

TABLE 1-continued

Sum formulas of suitable phyllosilicates[a]

| Nr. | Type | Empirical formula |
|---|---|---|
| 168 | Bementite | $Mn_7Si_6O_{15}(OH)_8$ |
| 169 | varennesite | $Na_8(Mn,Fe^{3+},Ti)_2[(OH,Cl)_2|(Si_2O_5)_5] \cdot 12H_2O$ |
| 170 | Naujakasite | $Na_6(Fe^{2+},Mn)Al_4Si_8O_{26}$ |
| 171 | manganonaujakasite | $Na_6(Mn^{2+},Fe^{2+})Al_4[Si_8O_{26}]$ |
| 172 | spodiophyllite | $(Na,K)_4(Mg,Fe^{2+})_3(Fe^{3+},Al)_2(Si_8O_{24})$ |
| 173 | sazhinite-(Ce) | $Na_2CeSi_6O_{14}(OH) \cdot nH_2O$ |
| 174 | sazhinite-(La) | $Na_3La[Si_6O_{15}] \cdot 2H_2O$ |
| 175 | burckhardtite | $Pb_2(Fe^{3+}Te^{6+})[AlSi_3O_8]O_6$ |
| 176 | tuperssuatsiaite | $Na_2(Fe^{3+},Mn^{2+})_3Si_8O_{20}(OH)_2 \cdot 4H_2O$ |
| 177 | palygorskite | $(Mg,Al)_2Si_4O_{10}(OH) \cdot 4H_2O$ |
| 178 | yofortierite | $Mn^{2+}_5Si_8O_{20}(OH)_2 \cdot 7H_2O$ |
| 179 | sepiolithe | $Mg_4Si_6O_{15}(OH)_2 \cdot 6H_2O$ |
| 180 | falcondoite | $(Ni,Mg)_4Si_6O_{15}(OH)_2 \cdot 6H_2O$ |
| 181 | loughlinite | $Na_2Mg_3Si_6O_{16} \cdot 8H_2O$ |
| 182 | kalifersite | $(K,Na)_5Fe_7^{3+}[(OH)_3|Si_{10}O_{25}]_2 \cdot 12H_2O$ |
| 183 | minehillite | $(K,Na)_{2-3}Ca_{28}(Zn_4Al_4Si_{40})O_{112}(OH)_{16}$ |
| 184 | truscottite | $(Ca,Mn)_{14}Si_{24}O_{58}(OH)_8 \cdot 2H_2O$ |
| 185 | orlymanite | $Ca_4Mn_3^{2+}Si_8O_{20}(OH)_6 \cdot 2H_2O$ |
| 186 | fedorite | $(Na,K)_{2-3}(Ca,Na)_7[Si_4O_8(F,Cl,OH)2|(Si_4O_{10})_3] \cdot 3.5H_2O$ |
| 187 | reyerite | $(Na,K)_4Ca_{14}Si_{22}Al_2O_{58}(OH)_8 \cdot 6H_2O$ |
| 188 | gyrolithe | $NaCa_{16}Si_{23}AlO_{60}(OH)_8 \cdot 14H_2O$ |
| 189 | tungusite | $Ca_{14}Fe_9^{2+}[(OH)_{22}|(Si_4O_{10})_6]$ |
| 190 | zeophyllite | $Ca_4Si_3O_8(OH,F)_4 \cdot 2H_2O$ |
| 191 | armstrongite | $CaZr(Si_6O_{15}) \cdot 3H_2O$ |
| 192 | jagoite | $Pb_{18}Fe^{3+}_4[Si_4(Si,Fe^{3+})_6][Pb_4Si_{16}(Si,Fe)_4]O_{82}Cl_6$ |
| 193 | hyttsjoite | $Pb_{18}Ba_2Ca_5Mn_2^{2+}Fe_2^{3+}[Cl|(Si_{15}O_{45})_2] \cdot 6H_2O$ |
| 194 | maricopaite | $Ca_2Pb_7(Si_{36},Al_{12})(O,OH)_{99} \cdot n(H_2O,OH)$ |
| 195 | cavansite | $Ca(VO)Si_4O_{10} \cdot 4H_2O$ |
| 196 | pentagonite | $Ca(VO)Si_4O_{10} \cdot 4H_2O$ |
| 197 | weeksite | $(K,Ba)_2[(UO_2)_2|Si_5O_{13}] \cdot 4H_2O$ |
| 198 | coutinhoite | $Th_{0.5}(UO_2)_2Si_5O_{13} \cdot 3H_2O$ |
| 199 | haiweeite | $Ca[(UO_2)_2|Si_5O_{12}(OH)_2] \cdot 6H_2O$ |
| 200 | metahaiweeite | $Ca(UO_2)_2Si_6O_{15} \cdot nH_2O$ |
| 201 | monteregianite-(Y) | $KNa_2YSi_8O_{19} \cdot 5H_2O$ |
| 202 | mountainite | $KNa_2Ca_2[Si_8O_{19}(OH)] \cdot 6H_2O$ |
| 203 | rhodesite | $KHCa_2Si_8O_{19} \cdot 5H_2O$ |
| 204 | delhayelite | $K_7Na_3Ca_5Al_2Si_{14}O_{38}F_4Cl_2$ |
| 205 | hydrodelhayelite | $KCa_2AlSi_7O_{17}(OH)_2 \cdot 6H_2O$ |
| 206 | macdonaldite | $BaCa_4Si_{16}O_{36}(OH)_2 \cdot 10H_2O$ |
| 207 | cymrite | $Ba(Si,Al)_4(O,OH)_8 \cdot H_2O$ |
| 208 | kampfite | $Ba_{12}(Si_{11}Al_5)O_{31}(CO_3)_8Cl_5$ |
| 209 | lourenswalsite | $(K,Ba)_2(Ti,Mg,Ca,Fe)_4(Si,Al,Fe)_6O_{14}(OH)_{12}$ |
| 210 | tienshanite | $(Na,K)_{9-10}(Ca,Y)_2Ba_6(Mn^{2+},Fe^{2+},Ti^{4+},Zn)_6(Ti,Nb)[(O,F,OH)_{11}|B_2O_4|Si_6O_{15}]_6$ |
| 211 | wickenburgite | $Pb_3CaAl[Si_{10}O_{27}] \cdot 3H_2O$ |
| 212 | silhydrite | $Si_3O_6 \cdot H_2O$ |
| 213 | magadiite | $Na_2Si_{14}O_{29} \cdot 11H_2O$ |
| 214 | stratlingite | $Ca_2Al[(OH)_6AlSiO_2(OH)_4] \cdot 2.5H_2O$ |
| 215 | vertumnite | $Ca_4Al_4Si_4O_6(OH)_{24} \cdot 3H_2O$ |
| 216 | zussmanite | $K(Fe^{2+},Mg,Mn)_{13}(Si,Al)_{18}O_{42}(OH)_{14}$ |
| 217 | coombsite | $K(Mn^{2+},Fe^{2+},Mg)_{13}[(OH)_7|(Si,Al)_3O_3|Si_6O_{18}]_2$ |

[a]cf. Mineral Atlas, mineral class VIII/H - phyllosilicates (phyllosilicates), Strunz 8 classification A very particularly preferred kind of bentonite is from the group of montmorillonites $((Na,Ca)_{0.3}(Al,Mg)_2Si_4O_{10}(OH_2.nH_2O)$. Bentonite is a mixture of different clay minerals and contains as its main ingredient montmorillonite. Sodium bentonite, for example, absorbs water, it can absorb a variety of its own dry weight. Furthermore, calcium bentonite can absorb fats and/or oils. In nature, there also is a type of bentonite that naturally contains petroleum.

The layered silicate micro- and/or nanoparticles described above are functionalized, non-functionalized, aggregated, unaggregated, agglomerated, non-agglomerated, supported and/or unsupported. For example, they may be functionalized, agglomerated and supported. But they can also be not functionalized and aggregated.

One of the montmorillonites is nanoclay. Nanoclays are derived from a large class of naturally occurring silicates, of which platy montmorillonites are most commonly used. Montmorillonite consists of approximately 1 nm thick aluminosilicate layers whose surface is substituted with metal ions and form the approximately 10 μη strong multilayer stacks. They are used, for example, as additives for plastics.

Usual and Well-Known Superabsorbents:

The superabsorber is preferably selected from the group consisting of copolymers of acrylic acid and/or methacrylic acid with alkali acrylate and/or alkali methacrylate, copolymers based on starch and acrylates and/or methacrylates and copolymers based on polyacrylamides and alkali acrylates and/or alkali methacrylates.

Superabsorbents are well-known substances and are produced annually on a 100,000 tons scale. Superabsorbents are mainly used as absorbent material in diapers.

When the devices of the invention are biocidal, they contain biocides such as
acaricides against mites,
algicides against algae,
bactericidal and bacteriostatic agents against bacteria and bacterial films,
fungicides against fungi,
insecticides against insects,
microbiocidal equipment against germs,
molluscicides against snails,
nematicides against roundworms and
virucide against viruses.

Examples of known biocides are 10, 10'-oxybisphenoxoarsine (OBPA), octylisothiazolinone (OIT), dichloroctylisothiazolinone (DCOIT), butylbenzisothiazolinone (BBIT), iodocarb (3-iodo-2-propynyl butylcarbamate), zinc pyrithione (zinc salt of pyridine-2-one). thiol-1-oxide), trichlosan (polychlorinated phenoxyphenols), silver ions and silver, especially in the form of silver nanoparticles.

Examples of known fungicides are DMI fungicides, QoI fungicides, dithiocarbamates, copper and sulfur, MBC fungicides, benzimidazoles and thiophanates, chloronitriles, dicarboimides, phenylamides, amines, AP fugicides, MBI fungicides, SDHI and decouplers.

However, polyoxometalates (POM) are particularly preferably used as biocides. The elemental composition and the structure of the POM particles is known, for example, the classification of POM in the following structures:

Lindquist-hexamolybdataion, $Mo_6O_{19}^{2-}$,
Decavanadatanion, $V_{10}O_{28}^{6-}$,
Paratungstatanion B, $H_2W_{12}O_{42}^{10-}$,
Mo36-polymolybdate, $Mo_{36}O_{112}(H_2O)^{8-}$,
Strandberg-structure, $HP_2Mo_5O_{23}^{4-}$,
Keggin-structure, $XM_{12}O_{40}^{n-}$,
Dawson-structure, $X_2M_{18}O_{62}^{n-}$,
Anderson-structure, $XM_6O_{24}^{n-}$,
Allman-Waugh-structure, $X_{12}M_{18}O_{32}^{n-}$,
Weakley-Yamase-structure, $XM_{10}O_{36}^{n-}$, and
Dexter-Silverton-structure, $XM_{12}O_{42}^{n-}$.

The n-superscript here is an integer from 3 to 20 and denotes the valency of an anion, which varies depending on the variables X and M.

As a further ordering principle for POM, formulas I to XIII can be of use:

$$(BW_{12}O_{40})^{5-} \quad (I),$$

$$(W_{10}O_{32})^{4-} \quad (II),$$

$$(P_2W_{18}O_{62})^{6-} \quad (III),$$

$$(PW_{11}O_{39})^{8-} \quad (IV),$$

$$(SiW_{11}O_{39})^{8-} \quad (V),$$

$$(HSiW_9O_{34})^{9-} \quad (VI),$$

$$(HPW_9O_{34})^{8-} \quad (VII),$$

$$(TM)_4(PW_9O_{34})_2{}^{t-} \quad (VIII),$$

$$(TM)_4(P_2W_{15}O_{56})^t \quad (IVX),$$

$$(NaP_5W_{30}O_{110})^{14-} \quad (X),$$

$$(TM)_3(PW_9O_{34})_2{}^{12-} \quad (XI) \text{ and}$$

$$(P_2W_{18}O_6)^{6-} \quad (XII).$$

In the formulas I to XII, TM is a divalent or trivalent transition metal ion such as Mn, Fe, Fe, Co, Co, Ni, Cu and Zn. The superscript t is an integer and indicates the valence of an anion, the dependency on the valency of the variable TM varies.

Furthermore, POM of the general formula XIII come into consideration:

$$(A_xGa yNb_aO b)z- \quad (XIII).$$

In the formula XIII, the variable A stands for phosphorus, silicon or germanium and the index x stands for 0 or for an integer from 1 to 40. The subscript y stands for an integer from 1 to 10, the subscript a stands for an integer from 1 to 8 and the subscript b is an integer from 15 to 150. The z factor varies depending on the nature and the degree of oxidation of the variable A. Also suitable are the aqua complexes and active fragments of POM XIII.

When the index x is 00, y is preferably equal to 6-a, where the index a is an integer from 1 to 5 and the index b is 19.

When the variable A is silicon or germanium, the index x is 2, the index y is 18, the index a is 6 and the index b is 77.

When the variable A is P, the index x is 2 or 4, the index y is 12, 15, 17 or 30, the index a is 1, 3, or 6 and the index b is 62 or 123.

Preferably, the anions I to XIII are applied in the form of salts with cations which are approved for cleansing and personal care and pharmaceutical use. Examples of suitable cations are $H^+$, $Na^+$, $K^+$, $NH_4^+$, and triethanolammonium monocations of naturally occurring amino acids such as histidinium (HISH *), arginium (ARGH +), or lysinium (LYSH *) or oligo- or polypeptides having one or more protonated basic amino acid residues.

[see U.S. Pat. No. 6,020,369, column 3, line 6, to column 4, line 29]

Very particularly preferred are $H_4[Si(W_3O_{10})_4]xH_2O$ (CAS-Nr. 12027-43-9) and $H_3[P(W_3O_{10})_4]xH_2O$ (CAS-Nr. 12501-23-4) and/or their salts.

The POM particles can be prepared by conventional and well-known wet chemical methods. However, it is also possible to dissolve the POM in water and to spray the resulting solution against a warm stream of air. In addition, it is possible to evaporate the solution in vacuo, irradiated with IR radiation.

The POM micro- and/or nanoparticles described above are functionalized, non-functionalized, aggregated, unaggregated, agglomerated, non-agglomerated, supported and/or unsupported. For example, they may be functionalized, agglomerated and supported. But they can not be aggregated.

Furthermore, because of his general expertise, one skilled in the art can readily identify other possible POMs.

may further contain.

Furthermore, the materials can also be treated with bleaching agents. Preference is given to chalk, talc, montmorillonite, clay minerals, papers, paper-like materials and/or titanium dioxide. This has the advantage that the materials retain their positive properties, but are now white and therefore more versatile.

Other Possible Additives:

glitter such as quarry, stone meal, pearly nut break, shell fracture, mica, pyrite, broken glass, gold leaf, potsherds and/or fragments of broken glass, diatomaceous earth natural pigments such as pigments from stones, clay, slate, shellac and/or lava stone cork, expanded cork dyes, colored pigments, white pigments, fluorescent pigments, natural pigments and phosphorescent pigments (phosphorus) Cement, foam cement, concrete, gypsum, lime red ribbon siligur and/or silica gel kefir, yogurt, other dairy products and beer sugar creatine salts, in particular common salts and/or alum salt buffers, acids, bases, also as a pretreatment for the starting materials nano silver flame retardant fabrics nano- and/or microcellulose chitin parts of insects water glass and horn shavings The materials and molded parts can be treated with various oils, in particular walnut oil. For example, the walnut oil can be mixed with color pigments and/or white pigments overnight so that the color pigments in the walnut oil dissolve. The walnut oil with the dissolved color pigments can now be applied, for example, on a cork surface, for example using a cloth.

In addition, papers and/or paper-like materials which are likewise enriched with fillers and/or other additives may be used for binding the carbon nanoparticles, carbon microparticles and/or carbon macroparticles in the materials. The papers and/or paper-like materials may be coloring, self-adhesive and/or a carrier material.

The preparation of the materials and the molded parts can be done by conventional and known methods.

In this case, wood chips, shredded biodegradable fibers, shredded biodegradable films and/or crushed separated manure and the carbon particles described above and optionally further additives, binders and/or fillers in various concentrations among the wood chips minced biodegradable fibers, shredded biodegradable films and/or crushed separated manure are mixed. To obtain a homogeneous mass, water can be added. Depending on the material, different amounts of water can be added. The resulting mixtures are homogenized, for example by grinding, extrusion or kneading. For shaping, the resulting homogenized mixtures are placed in molds and pressed under high pressure, optionally at higher temperatures. The water is volatilized from the homogenized mixture and/or it is a compound with the additives, adhesives and/or fillers. After pressing, the optionally still moist molded parts are dried, for example, in ovens and or under IR radiation. The temperatures used depend primarily on the thermal stability of the molded parts.

The molded parts can also be produced by 3-D printing from fluid materials.

The blended, agitated and/or whisked materials can also be made into shapes, rolls, molds, casting, extruding, drawing, spraying, pressing, foaming, blowing and/or using pressure in layers, layers, upsetting, swelling and/or flooding be processed directly to devices according to the invention.

The mixing, stirring, whisking and/or pressing of the raw materials of the materials can be done by means of various devices such as ultrasound and/or Vibramix. In addition, the crushed starting products can be fractionated before processing only to then be put back together in one and/or more mixing ratios.

The individual starting materials of the materials can be pretreated before processing. For example, they may be prescanned, trimmed and/or wetted. This can be done at different times and/or lengths.

By different metals, the surfaces of the molded parts and/or the devices according to the invention can be modified. By the so-called alloying elements, the strength, hardness, corrosion resistance, toughness and/or fatigue strength can be increased.

The structure of the molded parts and the devices according to the invention may vary. It can be homogeneous and/or heterogeneous. Furthermore, it can have various large cavities, which can be arranged in different ways. These can be structured, not structured and/or partially structured.

To produce the devices according to the invention from the molded parts, a variety of methods can be used.

The Construction Process

In this method, the molded parts are built position by position, thus layer by layer. In this case, various connection materials and/or techniques are used. An example is a plate-shaped molding containing notches. These notches are worked layer by layer into the molded parts until the device according to the invention results. In this case, the stratification of the individual layers and/or layers may be homogeneous and/or heterogeneous.

Subtraction Process

In this method, the molded parts are processed with tools until the device according to the invention is obtained. An example is the device according to the invention when it contains notches. Here, the notches are incorporated after the completion of the plate-shaped molding.

Another example is the production of lattice or sieve-shaped molded parts and devices according to the invention by the removal of material.

3D Printing

In this method, the still fluid material is mixed and processed with other materials, such as adhesives, by means of 3D technology to the desired molded parts, which are then assembled to form the device according to the invention. Or the still fluid material is molded directly to form the device according to the invention using the 3-D technique.

Examples of devices according to the invention are board materials, composite materials and/or other composite materials.

The technical basics for board materials, composites and/or other composite materials are regulated in standards and/or approval limits. These are produced by a European technical board and/or a general construction supervisory board. The marking of the construction products differs according to the respective technical basics. The DIN standards also include the field of application, the performance characteristics, the fire behavior, the water vapor permeability, the thermal conductivity, strength and/or rigidity, the biological durability, the content of OCO, the labeling and/or the technical classes.

The scope of application defines the area of application through the composition of the board materials, composites and/or other composites. Performance characteristics are assessed by strength and/or stiffness characteristics. The fire behavior defines how the board materials, composite materials and/or other composite materials may behave in a fire. The water vapor permeability indicates how permeable the board materials, composites and/or other composites are. The thermal conductivity applies to the heat flow, which is measured at right angles to the fiber direction. The strength is determined by various values specified in different standards for the respective board materials, composites and/or other composites. Characteristics of the individual board materials, composites and/or other composite materials are given characteristic values for the design. Last but not least, the technical classes give an indication of the values of the board materials, composites and/or other composite materials.

In the case of wood materials, for example, a distinction is generally made between laminated wood, in which wood layers of boards and/or veneers are glued, where the fiber direction of inner layers and cover layers runs parallel, plywood, understood to mean a board of at least three layers glued together, whose fiber direction is at a right angle crossing, chipboard, bound with binder shavings of various sizes and/or arrangements, and/or fiber materials, which are pressed with wood fibers and binder to form materials.

The individual applications of the board materials, composites and/or other composite materials are divided into categories according to the European standards. These categories include dry, wet, outdoor, general purpose, load bearing and/or load duration.

The construction of such panel materials, composites and/or other composite materials is always asymmetric. The board materials, composites and/or other composites are dimensionally stable, and in an asymmetric system, for example in a three layer system, the outer layers have the same material thickness. Furthermore, there are source-stable and non-swellable board materials, composites and/or other composite materials.

The devices according to the invention can be further processed by various techniques, namely drilling, milling, sawing (positive and/or negative machining), grinding, bending, punching, lasers or water jets. The application of, for example, paint can be done by a casting process, UV-process, spraying, brushing and/or spraying. The veneering can be done by a vacuum method and/or by a membrane press.

Furthermore, the devices according to the invention can be subjected to further different treatments. Thus, for example, the surface of the devices according to the invention can be painted, stained, oiled, waxed, glazed, dipped, impregnated, laminated, laminated, veneered, printed, embossed, anodized, galvanized, enameled, glazed and/or rolled. Furthermore, the surface can be treated by vapor deposition and/or be covered by various methods. For this purpose, a variety of tools such as saws made of hard metal, also known as sintered metal and/or made of diamonds, used.

Since carbon particles have been added to the molded parts and the devices according to the invention, the functions of the devices according to the invention vary. The passive function of the materials according to the invention can be, for example, that the carbon particles bind various pollutants and/or other molecules by diffusion, effusion, adsorption and/or absorption. The active function of the materials according to the invention happens on the one hand by convection and on the other by currents. The convection is controlled by temperature differences in rooms and/or the currents by the draft, as after the Venturi and Stokes effect.

Furthermore, the devices according to the invention can be equipped with further additional materials and/or technical devices. These may include fans, for additional lift circulation, and/or solar systems for operating these fans.

The structure of the devices according to the invention can have different variants. First, they can be structured throughout and/or have gaps and/or holes through which the air can circulate. In addition, carbon filters and/or other air filters can be incorporated into the material according to the invention.

The compounds in the devices according to the invention can be very different. The list below shows types of connections and/or their materials, also called composite materials. The list is only an example and not fully listed. On the basis of his general knowledge, the expert can easily name further possible types of connection and/or their materials.

Types of Connection and/or Their Materials
Connection by means of traction:
nailing
screws
wedging
Connecting means for adhesion:
screw, bolt, wedge
fitting
nail, clamp, fixed wedge
Connection by means of fabric closure:
gluing paste
glue
embossing by thermal treatment
Connection means for the material bond:
hot melt adhesive
glue, gluing paste
Connection by means of positive locking
pins, dowels
springs, burrs
Connecting means for positive locking:
wedge, eccentric, feather key
fitting
glue, gluing paste Further examples of the compounds are exemplified below and not exhaustive. The person skilled in the art can readily enumerate further possible compounds on the basis of his general knowledge.

The devices according to the invention can also be slotted, chased, overlapped, wedged, milled, layered, doweled, sprung, butt-glued, rounded, folded over, profiled, screwed, pruned, over wedged, toothed, grilled, folded, nailed, grooved, screwed and/or be hung up.

The uses of the devices according to the invention are shown in the list below. The list is only an example and not fully inclusive. The person skilled in the art can, on the basis of his general knowledge, name without further, further possible applications.

Construction Field
Interior Construction Work:
frames
sound insulation
impact noise panels
installation panels
cork panels
cork tapestry
insulating mats
profile- and/or baseboards
fiberboards
thermal insulation
insulation by insufflation
bulk insulation
sandwich construction
partitions
ceiling panels
cork-based ceiling panels
countertops
concrete formwork
vapor barrier and air seal air conditioning systems
Exterior Construction Work:
façade panels
frame construction
molded parts made of wood-concrete
load-bearing and/or stiffening planking in timber construction
wall, ceiling and roof panels
roofing
lightweight
Furniture Industry:
base plates
cover plates
shelves
rear walls
cheeks and/or rims
fronts and/or doors
wreath profiles
wood-concrete
cabinet walls
seating furniture
paravan
umber
Transport and Logistics:
crate and/or pallet industry
partitions in boxes
Automobile Industry:
guide posts
vehicle construction, for example for interior lining
Aircraft Construction and Shipbuilding:
as composite materials
Gaming Equipment
table tennis table
wooden concrete frames
Other Applications:
wood wool lightweight panels
pellet industry
wood briquettes
pulp and/or wood pulp
soundproof walls made of wood-concrete
packaging It is understood that the features mentioned above and explained in more detail below can be used not only in the specified combinations and configurations, but also in other combinations and configurations or alone, without departing from the scope of the present invention.

BRIEF DESCRIPTION OF THE FIGURES

The invention will now be explained in more detail by means of exemplary embodiments, reference being made to the attached FIGS. 1a to 8. In a simplified, not to scale representation.

Figure 1A:
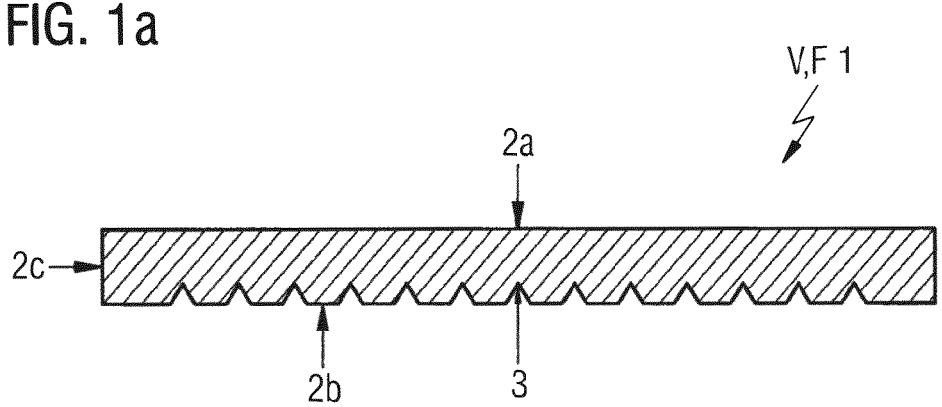
FIG. 1a shows a view of a longitudinal section through a shelf V 1 with notches 3.

In the FIGS. 1a to 8, the reference numerals have the following meaning:
1 shelf
2a smooth surface of 1
2b notched surface of 1
2c, 2d side edges
3 notch
4 partition wall
5a side surfaces of 4
5b side edges of 4
6 vertical holes
7 top edge of 4
8 door leaf
9 upper edge of 8
10 lower edge of 8
11a, b side edges of 8
12 door area
13 cutout from 12
14 perforated grids
15 ceiling panels
16 inner surface of 15
17 outer surface of 15
18 side edge of 15
19 puncture
20 electric fans
21 electrical connections
22 airflow
23 upper area of a door leaf
23.1 rotating counterpart to the door frame
23.2 outside of the door leaf
23.3 inside of the door leaf
23.4 upper horizontal section of the peripheral edge of the door leaf
23.5 circumferential stop surface on the door frame
23.6 circumferential top edge of 23.1
24 cutout
24.1 surrounding bearing surface
25 air-permeable bag for molded parts F
26 cover plate
26.1 gas passage
27 countersunk
27.1 screw head
28 tube
28.1 pipe wall
29 loose bed
30 air flow
V device
F molded part of the material to be used according to the invention Preparation Example 1

The Preparation of a Material 1

Waste wood chips and separated manure, which was disinfected and sterilized by placing it in saline, were mixed in a weight ratio of 2:1. The mixture was crushed with a turbo mill. Thereafter, to this comminuted mixture, 0.5 wt.-% $H_4[Si(W_3O_{10})_4]xH_2O$ as biocide and 30 wt.-% biochar having an average particle size of 100 μm was added. The mixture was slurried with a little water, further comminuted in a ball mill and homogenized. Subsequently, the homogenized mixture was dried to a water content of 10 wt.-%. The weight percentages given above are based on the total amount of the mixture. The water content served to improve the processability of the resulting mixture of wood, separated manure, biocide and biochar. The material could easily be stored, transported and processed until further use. It was completely odorless and was not affected by prolonged storage of microorganisms.

Preparation Example 2

The Preparation of a Material 2

Separated manure, which had been disinfected and sterilized by placing it in saline, was comminuted with a turbo mill. Thereafter, to the comminuted separated manure 0.5 wt.-% $H_4[Si(W_3O_{10})_4]xH_2O$ as biocide and with 30 wt.-% biochar was added. The mixture was slurried with dilute water, further comminuted in a ball mill and homogenized. Subsequently, the homogenized mixture was dried to a water content of 10 wt.-%. The weight percentages given above are based on the total amount of the mixture. The water content served to improve the processability of the resulting mixture of separated manure, biocide and biochar. The material could easily be stored, transported and processed until further use. It was completely odorless and was not affected by prolonged storage of microorganisms.

DETAILED DESCRIPTION OF THE FIGURES

Figure 1B:
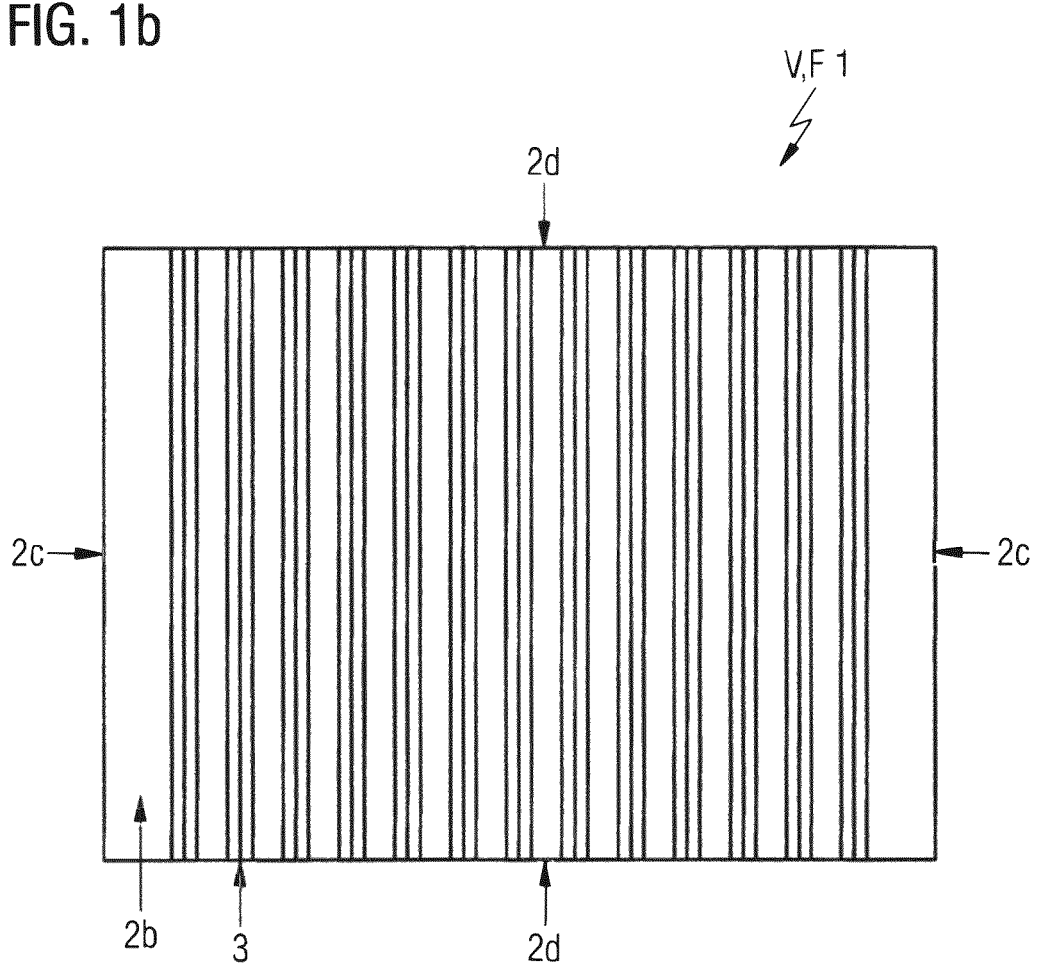
FIG. 1b shows a top view of notched side 2b of the shelf V 1 with the notches 3.

FIGS. 1a and 1b

FIG. 1a shows a plan view of a longitudinal section through a shelf 1 with notches 3. FIG. 1b shows a plan view of the notched side 2b of the shelf 1 with the notches 3.

The shelf V 1 was made of the material 1 of Preparation Example 1 through pressing at high pressure.

The shelf V 1 had a smooth surface 2a, which could also have notches 3 if necessary. In the notched surface 2b of the shelf 1, the notches 3 were milled. Due to the notches, the surface 2b was larger and could now absorb more pollutants and/or VOC. Furthermore, the air could circulate through the notches 3 and thus be cleaned of VOC, pollutants microorganisms.

FIG. 2

Figure 2:
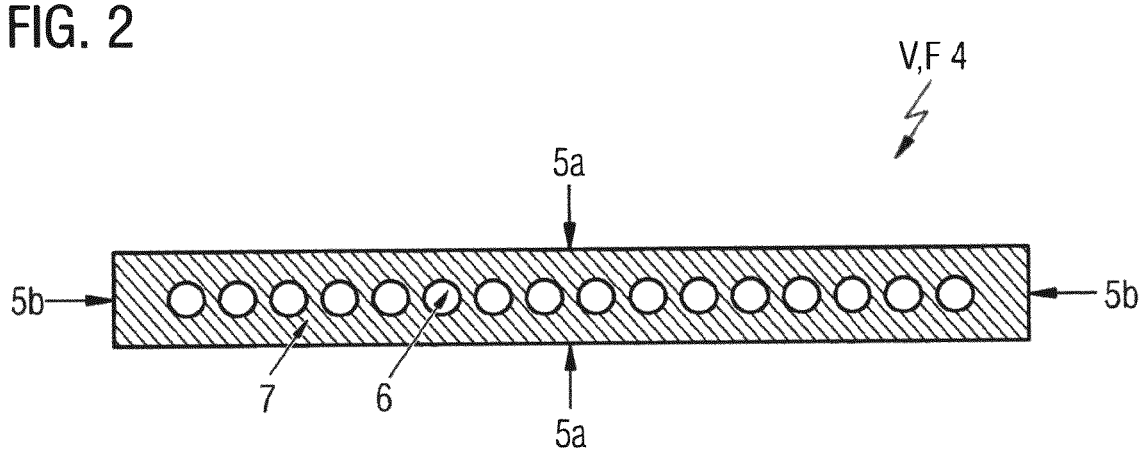
FIG. 2 shows a plan view of the upper edge 7 of the partition wall V 4 with vertical holes 6.

FIG. 2 shows a plan view of the upper edge 7 of a partition 4 with vertical holes 6.

The partition V 4 was made of the material 1 of Preparation Example 1 through pressing at high pressure. The partition V 4 had vertical holes 6. Through the vertical holes 6, the surface of the partition V 4, but especially the carbon, was larger, and this could now absorb more pollutants and/or VOC. Furthermore, the air could circulate through the holes 6 and thus be cleaned of VOC, pollutants and microorganisms.

FIG. 3

Figure 3:
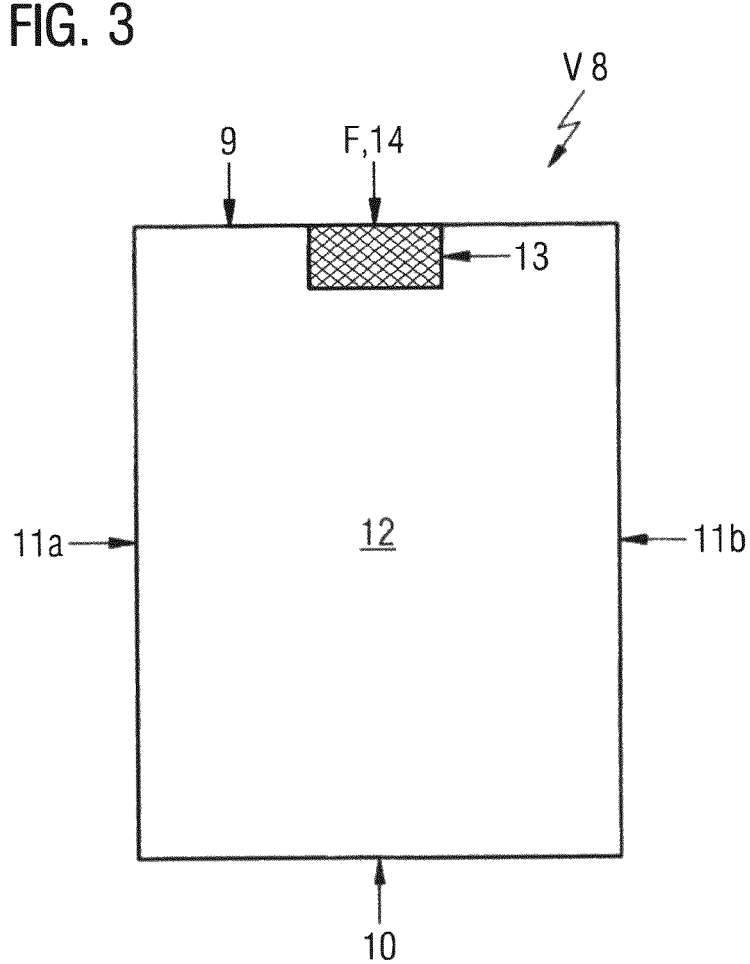
FIG. 3 shows a plan view of the door surface 12 of a door panel V 8 with the cutout 13 and the perforated grid F 14.

FIG. 3 shows the plan view of a door surface 12 of a door leaf 8 with an upper edge 9, a lower edge 10 and two side edges 11a and 11b. In the door surface 12 a rectangular piece was milled out at the top edge 9, the cutout 13. It was dimensioned such that a perforated grid 14 made of material 1 of Production Example 1, produced through pressing at high pressure, could be fitted as an exchangeable carbon filter insert. The perforated grid 14 was able to absorb pollutants and/or VOC from the air stream through which it flowed. In addition, they were biocidal.

FIG. 4

Figure 4:
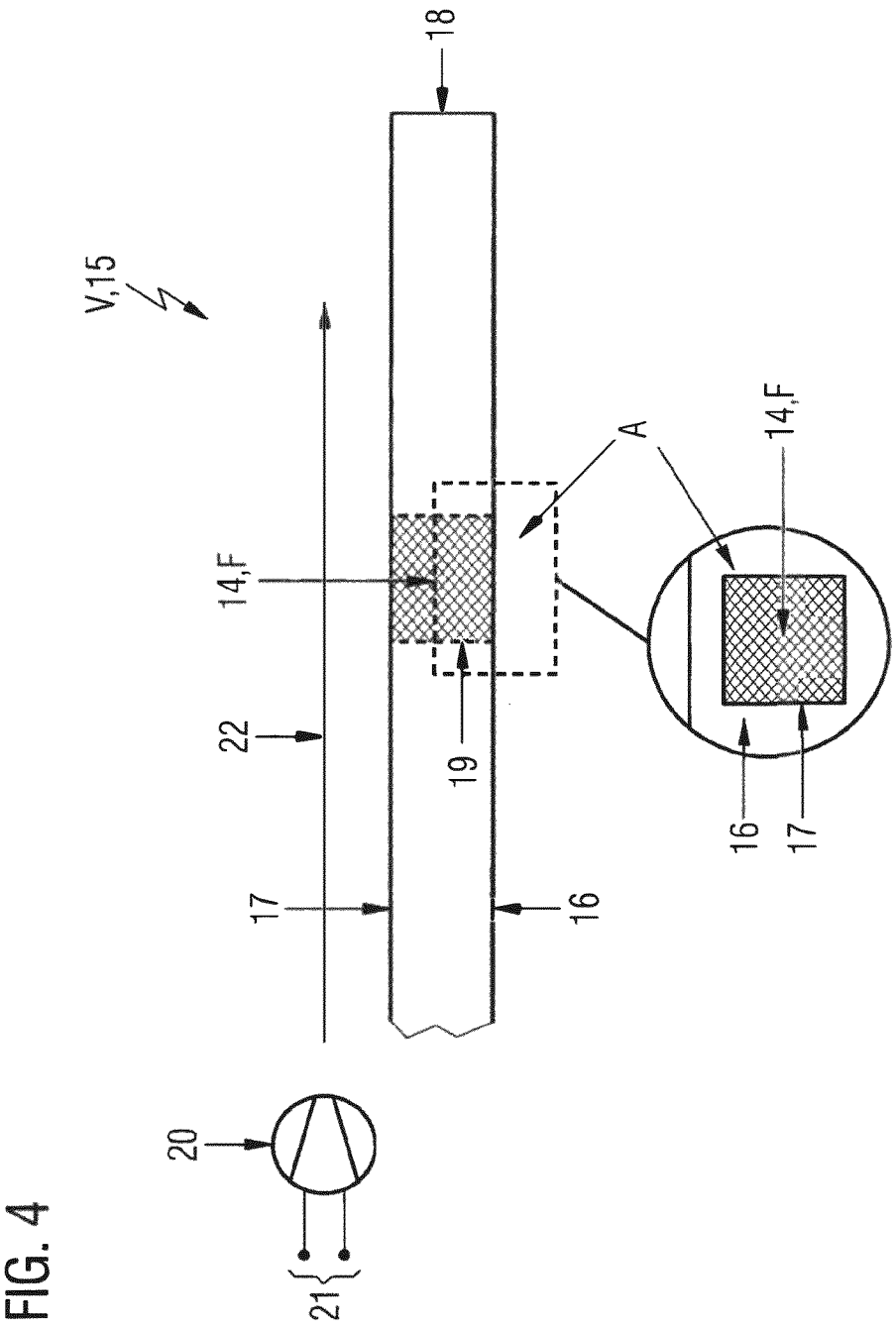
FIG. 4 shows a plan view of a longitudinal section through a ceiling panel V 15 with a through hole 19 with a perforated grid F 14 and a plan view of a section A on the inner surface.

FIG. 4 shows a plan view of a longitudinal section through a ceiling panel 15 with a through bore 19 with a perforated grid 14, as described in FIG. 3, and a plan view of a cutout A on the inner surface 16 of the ceiling panel 15.

The ceiling panels 15 further have an outer surface 17 and side edges 15. Behind the outer surface 17, an air flow 22 was moved by an electric fan 20. The electric fan 20 was connected via the electrical connections 21 to a solar cell.

Through these ceiling panels 15, the indoor air could be effectively cleaned of pollutants and/or VOC. In addition, they were biocidal.

Figure 5:
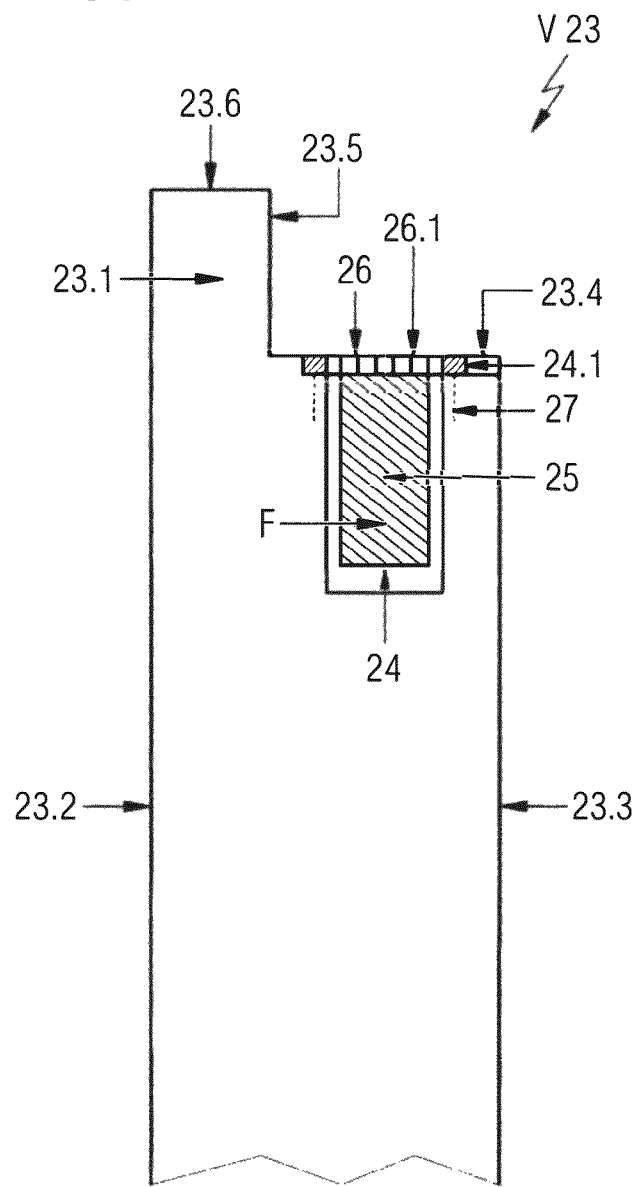
FIG. 5 shows a plan view of the longitudinal section through the upper portion of a door panel V 23 with the cutout 24 and the bag 25 for molded parts F.
Figure 6:
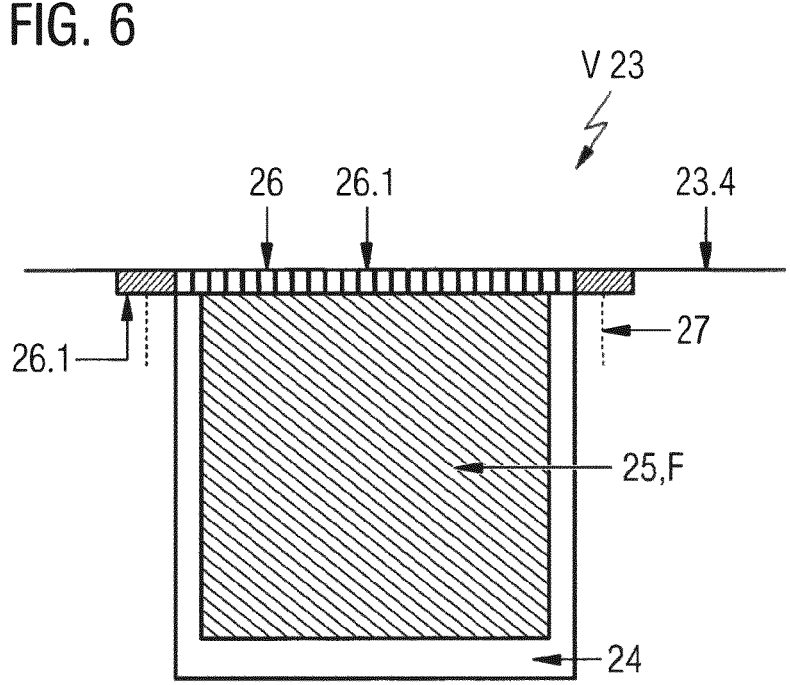
FIG. 6 shows a plan view of the cross section of the door panel V 23 in the region of the cutout 24 and the bag 25 for molded parts F.
Figure 7:
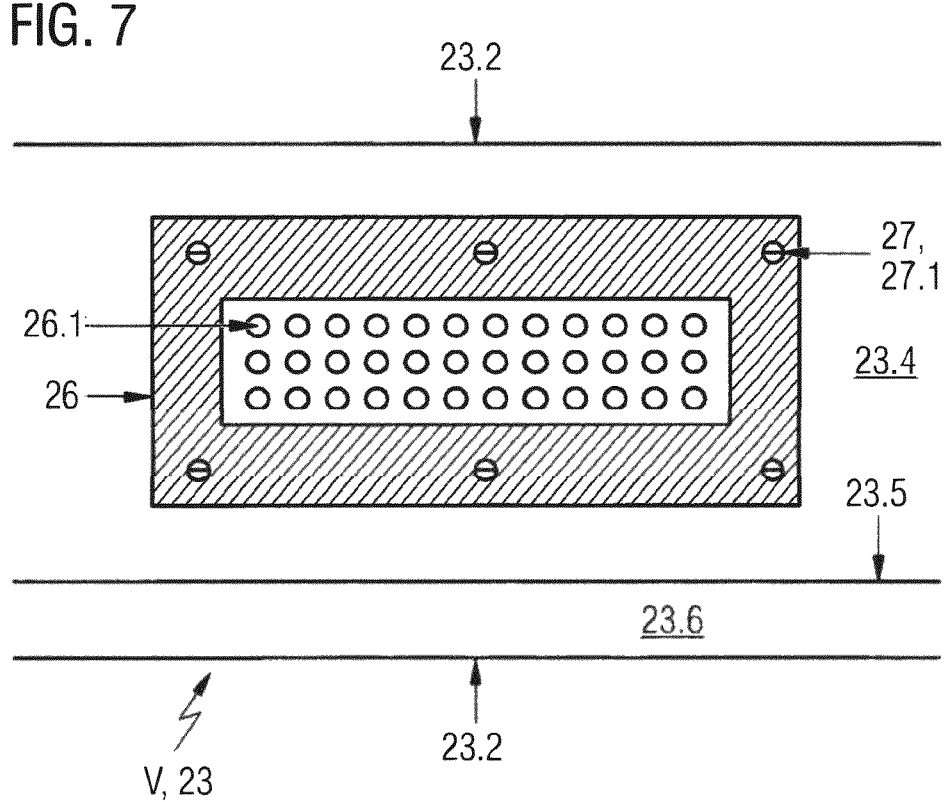
FIG. 7 shows a plan view of the upper edge of the door leaf V 23 in the region of the cover plate 26.

FIGS. 5 to 7

FIG. 5 shows a plan view of the longitudinal section through the upper region of a door leaf V, 23.

FIG. 6 shows a plan view of the cross section through the upper region of the door leaf V, 23.

The figure numeral 7 shows a plan view of the upper edge of the door leaf upper horizontal portion of the peripheral edge of the door leaf V, 23 in the region of the cover plate 26

The upper portion 23 of the door leaf 23 had an outer side 23.2 and an inner side 23.3 and a door leaf V, 23 circumferential counterpart 23.1 to the door frame with a circumferential stop surface 23.5 to the door frame and a peripheral upper edge 23.6. The door leaf V, 23 was essentially made of pressed chipboard and had ventilation slots and ventilation holes on the lower edge.

In the upper horizontal portion 23.4 of the peripheral edge of the door panel V, 23 a cutout 23.4 was centrally arranged, which had a peripheral bearing surface 24.1 for the cover plate 26 made of stainless steel. The cover plate 26 had except for the section with which it serves on the rotating support surface 24.1, holes as air passage 26.1. In the area of the peripheral bearing surface 24.1, the cover plate 26 was secured with countersunk screws 27, 27.1 made of stainless steel.

On the inside of the cover plate, a bag 25 was attached. The bag 25 consisted of a close-meshed network of cotton fibers and contained spherical shaped parts F of a diameter of 0.5 cm from the material 2 of Preparation Example 2.

By means of this device V, 23, 25, F according to the invention, it was possible to remove the VOC and pollutants still present in the door leaf 23. In addition, the door frame in contact with the door leaf 23 could also be freed of these pollutants. The same applied to the room air circulating through and around the inventive device V, 23, 25, F. In addition, the spherical molded parts F had biocidal properties.

FIG. 8

Figure 8:
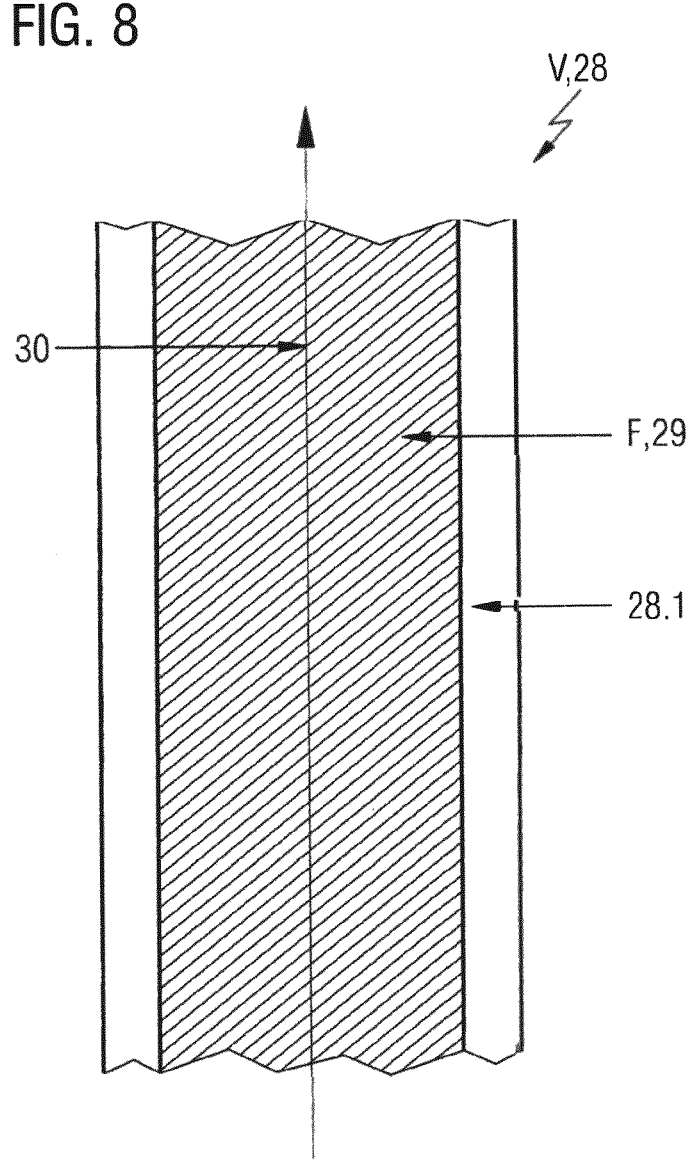
FIG. 8 shows a plan view of the longitudinal section through a tube V 28 with a packed bed 29 of molded parts F.

FIG. 8 shows a longitudinal section through a pipe V, 28 according to the invention with a pipe wall 28.1 made of hardwood. The tube V, 28 had a packed bed 29. The bulk bed 29 consisted of Raschig rings as molded parts F. The Raschig rings were made of the material 2 of Preparation Example 2. The bulk bed 29, F was flowed through by an air flow 30 in the arrow direction, the air was freed from VOC, pollutants and microorganisms. The tube V, 28 according to the invention was therefore ideal for use in air conditioning systems.

A decisive advantage of the devices V according to the invention according to FIGS. 1 to 8 was given by their compostability.

The invention claimed is:

1. A material comprising a homogeneous mixture of:
   (i) carbon particles and separated liquid manure sanitized and rendered sterile by immersion in saline, or
   (ii) carbon particles, wood and separated liquid manure sanitized and rendered sterile by immersion in saline,
   the material being a gas permeable and volatile organic compounds (VOC) and pollutants absorbing panel material or a composite material,
   the carbon particles being nanoparticles, microparticles and/or macroparticles,
   the carbon particles having a regular, irregular, free, aggregated and/or agglomerated geometrical arrangement in the homogeneous mixture.

2. The material according to claim 1, wherein
   the carbon nanoparticles have an average particle size of 1 nm to <1000 nm,
   the carbon microparticles have an average particle size of >1000 nm to <1000 µm and the carbon macroparticles have an average particle size of 1000 µm.

3. The material according to claim 2, wherein the carbon is selected from the group consisting of biocarbons, biochar, charcoal, screening residues of charcoal, wood ash, activated carbons, hard coal, animal charcoal, carbons from animal waste, pyrogenic carbon having different degrees of pyrolysis, functionalized carbons, pretreated carbons, washed carbons, and extracted carbons.

4. The material according to claim 3, wherein the carbon and the biocarbons comprise carbon structures resulting from intense heating of organic and/or ligninous material.

5. The material according to claim 4, wherein the carbon is selected from the group comprising one or more of functionalized carbon, surface-modified carbon, crushed carbon, dried and moistened carbon, and crushed and partially dried carbon.

6. The material according to claim 1, further containing additives selected from the group consisting of additives, excipients, fillers, adhesives, reinforcing fibers flame retardants, plastics, dampening materials, insulating materials, desiccants, superabsorbents, phylosilicates, nanoclay, kieselguhr, zeolites, biocides, dyes, colored pigments, white pigments, fluorescent pigments, natural pigments, phosphorescent pigments, glitter, cork, cement, foam cement, concrete, gypsum, lime base, rotband, kefir, yoghurt, dairy products, beer, sugar, creatine, salts, nanocellulose, microcellulose, water glass, horn shavings and oils.

7. The material according to claim 6, wherein the biocides are polyoxometalates (POM).

8. The material according to claim 7, wherein the polyoxometalates are micro- and/or nanoparticles, which are agglomerated, not agglomerated, functionalized, non-functionalized, aggregated, not aggregated, supported and/or not supported.

9. A method comprising:
   using the material of claim 1 for purification of pollutants and/or or other substances.

10. A method comprising:
    using the material of claim 1 in building construction for interior and exterior construction, in furniture industry, in transport and logistics, in automotive industry, in aircraft construction and in gaming equipment.

* * * * *